US012605402B2

(12) United States Patent (10) Patent No.: US 12,605,402 B2
Reiner et al. (45) Date of Patent: Apr. 21, 2026

(54) THERAPEUTIC USES OF OXIDIZING HYPOTONIC ACID SOLUTIONS

(71) Applicant: APR Applied Pharma Research SA, Geneva (CH)

(72) Inventors: Giorgio Reiner, Como (IT); Paolo Galfetti, Balerna (CH); Roberto De Noni, Balerna (CH)

(73) Assignee: APR Applied Pharma Research SA, Geneva (CH)

( * ) Notice: Subject to any disclaimer, the term of this patent is extended or adjusted under 35 U.S.C. 154(b) by 921 days.

(21) Appl. No.: 17/597,220

(22) PCT Filed: Jul. 2, 2020

(86) PCT No.: PCT/IB2020/056277
    § 371 (c)(1),
    (2) Date: Dec. 29, 2021

(87) PCT Pub. No.: WO2021/001789
    PCT Pub. Date: Jan. 7, 2021

(65) Prior Publication Data
    US 2022/0241324 A1      Aug. 4, 2022

Related U.S. Application Data

(60) Provisional application No. 62/937,885, filed on Nov. 20, 2019, provisional application No. 62/937,884, filed on Nov. 20, 2019, provisional application No. 62/935,283, filed on Nov. 14, 2019, provisional application No. 62/870,100, filed on Jul. 3, 2019, provisional application No. 62/870,096, filed on Jul. 3, 2019.

(51) Int. Cl.
    *A61K 33/20*      (2006.01)
    *A61K 9/00*      (2006.01)
    *A61K 9/08*      (2006.01)
    *A61K 31/445*      (2006.01)
    *A61K 31/4709*      (2006.01)
    *A61K 31/496*      (2006.01)
    *A61K 31/7036*      (2006.01)
    *A61K 31/7048*      (2006.01)
    *A61K 45/06*      (2006.01)
    *A61P 17/02*      (2006.01)
    *A61P 31/14*      (2006.01)

(52) U.S. Cl.
    CPC ............ *A61K 33/20* (2013.01); *A61K 9/0014* (2013.01); *A61K 9/0043* (2013.01); *A61K 9/08* (2013.01); *A61K 31/445* (2013.01); *A61K 31/4709* (2013.01); *A61K 31/496* (2013.01); *A61K 31/7036* (2013.01); *A61K 31/7048* (2013.01); *A61K 45/06* (2013.01); *A61P 17/02* (2018.01); *A61P 31/14* (2018.01)

(58) Field of Classification Search
    CPC .... A61K 33/20; A61K 9/0014; A61K 9/0043; A61K 9/08; A61K 31/445; A61K 31/4709; A61K 31/496; A61K 31/7036; A61K 31/7048; A61K 45/06; A61P 31/14; A61P 17/02
    See application file for complete search history.

(56) References Cited

U.S. PATENT DOCUMENTS

| | | | | |
|---|---|---|---|---|
| 11,517,526 B2 * | 12/2022 | Walker | .................. | A61Q 19/00 |
| 2004/0062818 A1 * | 4/2004 | Calderon | ................ | A61P 11/02 |
| | | | | 424/661 |
| 2015/0231173 A1 * | 8/2015 | Sampson | ............... | A61K 47/02 |
| | | | | 424/661 |
| 2016/0271172 A1 * | 9/2016 | Sampson | ................. | A61K 9/06 |
| 2017/0360832 A1 * | 12/2017 | Sampson | ............... | A61K 33/20 |
| 2019/0167717 A1 * | 6/2019 | Sampson | ............... | A01N 59/08 |

FOREIGN PATENT DOCUMENTS

| | | | | |
|---|---|---|---|---|
| CN | 106943429 A | 7/2017 | | |
| JP | 2000226680 A | 8/2000 | | |
| WO | WO-03028741 A1 * | 4/2003 | ............. | A23L 3/358 |
| WO | WO-2007048772 A1 | 5/2007 | | |
| WO | WO-2008089268 A2 | 7/2008 | | |
| WO | WO-2008131936 A2 * | 11/2008 | ............. | A61K 33/00 |
| WO | WO-2016100543 A2 | 6/2016 | | |
| WO | WO-2021001789 A1 | 1/2021 | | |

OTHER PUBLICATIONS

Burch, J., et al., "Kindler syndrome: a new mutation and new diagnostic possibilities," Arch Dermatol 142(5) pp. 620-624, Springer, Germany (May 2006).
Cialfi, S., et al., "The loss of ATP2C1 impairs the DNA damage response and induces altered skin homeostasis: Consequences for epidermal biology in Hailey-Hailey disease," Sci Rep 6:31567, 11 pages, Springer, Germany (Aug. 2016).
Denyer, J., et al., "Best Practice Guidelines: Skin and wound care in epidermolysis bullosa," An International Consensus. Wounds International 2017, United Kingdom, accessed at https://www.woundsinternational.com/resources/details/best-practice-guidelines-skin-and-wound-care-in-epidermolysis-bullosa, 60 pages (2017).
Fine, J.D., et al., "The classification of inherited epidermolysis bullosa (EB): Report of the Third International Consensus Meeting on Diagnosis and Classification of EB," J Am Acad Dermatol 58(6) pp. 931-950, Elsevier, Netherlands (Jun. 2008).
Kasperkiewicz, M., et al., "Epidermolysis Bullosa Acquisita: From Pathophysiology to Novel Therapeutic Options," J Invest Dermatol 136(1) pp. 24-33, Elsevier, Netherlands (Jan. 2016).
(Continued)

*Primary Examiner* — Robert A Wax
*Assistant Examiner* — Olga V. Tcherkasskaya
(74) *Attorney, Agent, or Firm* — Sterne, Kessler, Goldstein & Fox P.L.L.C.

(57) ABSTRACT

Methods for treating or preventing ulcers caused by Epidermolysis Bullosa ("EB"), EGFR inhibitor-induced skin toxicities, lesions caused by Hailey-Hailey Disease ("HHD"), Buruli Ulcers, and SARS-CoV-2 infections, by topically applying a hypotonic, acid oxidizing solution containing hypochlorous acid (HClO) to the affected area.

22 Claims, 5 Drawing Sheets

(56) References Cited

OTHER PUBLICATIONS

Kensler, T.W., et al., "Cell survival responses to environmental stresses via the Keap1-Nrf2-ARE pathway," Annu Rev Pharmacol Toxicol 47 pp. 89-116, Annual Reviews Inc., United States (2007).

Laimer, M., et al., "Hereditary epidermolysis bullosa," J Dtsch Dermatol Ges 13(11) pp. 1125-1133, Wiley, United States (Nov. 2015).

Moi, P., et al., "Isolation of NF-E2-related factor 2 (Nrf2), a NF-E2-like basic leucine zipper transcriptional activator that binds to the tandem NF-E2/AP1 repeat of the beta-globin locus control region," Proc Natl Acad Sci 91(21) pp. 9926-9930, National Academy of Sciences, United States (Oct. 1994).

Zhang, "Mechanistic Studies of the Nrf2-Keap1 Signaling Pathway," Drug Metab Rev. 38(4):769-89, Marcel Dekker, United States (2006).

Wang, L., et al., "Hypochlorous Acid as a Potential Wound Care Agent," Journal of Burns and Wounds vol. 6:e5: 65-79, Open Science Co., United States (Apr. 2007).

Sakarya, S., et al., "Hypochlorous Acid: An Ideal Wound Care Agent with Powerful Microbicidal, Antibiofilm, and Wound Healing Potency," Wounds 26(12):342-350 (Nov. 2014).

Sergeev, P. V., "A Short Course in Molecular Pharmacology," pp. 10, Moscow, (1975).

Kholodov, L.E., et al., "Clinical Pharmacokinetics," pp. 83-98, 134-138, 160, 378- 380, Moscow (1985).

Office Action mailed Dec. 12, 2023 in Russian Patent Application No. 2022102493, Reiner, G., et al., filed Jul. 2, 2020, 2 pages.

* cited by examiner

THERAPEUTIC USES OF OXIDIZING HYPOTONIC ACID SOLUTIONS

FIELD OF THE INVENTION

The present invention relates to methods for treating or preventing ulcers caused by Epidermolysis Bullosa ("EB"), EGFR inhibitor-induced skin toxicities, lesions caused by Hailey-Hailey Disease ("HHD"), Buruli Ulcers, and SARS-CoV-2 infections, by topically applying a hypotonic, acid oxidizing solution containing hypochlorous acid (HClO) to the affected area.

BACKGROUND OF THE INVENTION

Various disorders of the skin of both natural and man-made origin are in need of an effective treatment, including ulcers caused by epidermolysis bullosa, EGFR inhibitor-induced skin toxicities, lesions caused by Hailey-Hailey Disease, and Buruli Ulcers.

EB is a heterogeneous group of rare, genetic skin disorders which cause the skin to blister and tear at the slightest touch. Those born with EB have skin so fragile they are called 'butterfly children'—their skin is quite simply as fragile as the wing of a butterfly. Painful open wounds and sores form where this exceptionally fragile skin is damaged—in some cases, internal linings and organs are also affected. Complications as a result of secondary infection and extensive scarring are factors that people living with EB often have to face. Tragically, certain types of EB can be fatal in infancy and others are severely life-limiting. EB may be inherited in either a dominant or recessive form. EB can also arise through a new spontaneous mutation—neither parent carries EB but the gene mutates spontaneously in either the sperm or the egg before conception. Rarely, a severe form of EB can be "acquired" as the result of autoimmune disease, where the body develops antibodies to attack its own tissue proteins.

Epidermal growth factor receptor (EGFR, also known as ErbB-1 or HER-1) is a protein that is found on the surface of some cells that causes cells to divide when epidermal growth factor binds to it. EGFR is found at abnormally high levels in cancer cells, and EGFR activation appears to be important in tumor growth and progression. EGFR is highly expressed on the epidermis, on the basal cell layer, at the level of the sebaceous glands and on keratinocytes. EGFR inhibitors bind to certain parts of the EGFR and slow down or stop cell growth. In cancer patients subjected to therapeutic schemes based on EGFR inhibitors, adverse reactions on the skin, such as papulopustular rash, paronychia, alteration of hair growth, itching and skin dryness, are commonly manifested as the aforementioned agents affect the skin cell proliferation process.

Hailey-Hailey disease is an autosomal dominantly inherited dermatosis first described by the brothers Hailey in 1939. The lack of ATP2C1 in keratinocytes leads to the loss of cell-to-cell adhesion (acantholysis) among the cells of the suprabasal layer of epidermis probably due to a retraction of keratin intermediate filaments from the desmosomal plaques. The disease is usually present in the third or fourth decade of life and is characterized by vesicular lesions, crusted erosions, and warty papules, that occur mainly on the neck and intertriginous areas and flexural areas of the skin. The disease is fully penetrant in adults but has a fluctuating course with variable expressivity. Management of this condition is difficult and existing treatments do not provide a long lasting positive therapeutic benefit. External factors such as sweating, UV exposure, friction, and super-infection with bacteria, fungi, and viruses play an important role in exacerbations and persistence of lesions.

Buruli Ulcer is a chronic debilitating disease that mainly affects the skin and sometimes bones. First described by Sir Albert Cook in 1897 in Uganda, it was not until the 1930s that Australian scientists led by Peter MacCallum first succeeded in culturing the organism from lesions of patients from the Bairnsdale region. Buruli Ulcer is caused by *Mycobacterium ulcerans* and belongs to the family of bacteria that causes tuberculosis and leprosy. Although the causative organism of Buruli Ulcer is an environmental bacterium, the mode of transmission to humans remains unknown. The organism produces a unique toxin—mycolactone—that causes the damage to the skin.

The SARS-CoV-2, is a respiratory virus with a close genetic similarity to bat coronaviruses. The SARS-CoV-2 is believed to spread primarily through droplets of saliva or discharge from the nose when an infected person coughs or sneezes. Most of the knowledge about the physicochemical properties of CoVs comes from SARS-CoV and MERS-CoV. SARS-CoV-2 can be inactivated by UV or heated at 56 C.° 30 min, and also sensitive to most disinfectants such as diethyl ether, 75% ethanol, chlorine, peracetic acid, and chloroform. At this time, there are no specific vaccines or treatments for SARS-CoV-2. However, there are many ongoing clinical trials evaluating potential treatments for the most severe forms but not yet a treatment for the entire population able to reduce and control the transmission of the virus.

STATEMENT OF NEED

There is an unmet medical need for safe and effective therapies for treating Epidermolysis Bullosa ("EB"), EGFR inhibitor-induced skin toxicities, lesions caused by Hailey-Hailey Disease ("HHD"), Buruli Ulcers, and SARS-CoV-2 infections. A fast, easy to use and safe treatment to treat the underlying pathogenesis of these conditions, and to speed wound care in the conditions affected by wounds, would greatly improve the quality of life of patients and their families afflicted by these conditions.

SUMMARY OF INVENTION

A hypotonic, acid oxidizing, aqueous solution defined by pH, chloride content, and free chlorine content has been developed with surprising versatility treating several defined topical conditions and respiratory infections. Thus, in a first principal embodiment the invention provides a method of treating a wound caused by Epidermolysis Bullosa ("EB") in a patient in need thereof comprising topically applying to said wound a therapeutically effective amount of a hypotonic, acid oxidizing, aqueous solution comprising a pH of from 2.5 to 6, a chloride content of less than 400 mg/L, and a free chlorine content of 20-140 mg/L, wherein said free chlorine content comprises $\geq 90$ w/w % hypochlorous acid (HClO), $\leq 10$ w/w % chlorine ($Cl_2$), and $\leq 3$ w/w % hypochlorite ($ClO^-$).

In a second principal embodiment the invention provides a method of treating an EGFR inhibitor-induced skin toxicity in a patient in need thereof comprising topically applying to skin affected by the skin toxicity a therapeutically effective amount of a hypotonic, acid oxidizing, aqueous solution comprising a pH of from 2.5 to 6, a chloride content of less than 400 mg/L, and a free chlorine content of 20-140 mg/L, wherein said free chlorine content comprises ≥90 w/w % hypochlorous acid (HClO), ≤10 w/w % chlorine (Cl$_2$), and ≤3 w/w % hypochlorite (ClO$^-$).

In a third principal embodiment the invention provides a method of treating a topical disorder caused by Hailey-Hailey disease ("HHD") in a patient in need thereof comprising topically applying to skin affected by said disorder a therapeutically effective amount of a hypotonic, acid oxidizing, aqueous solution comprising a pH of from 2.5 to 6, a chloride content of less than 400 mg/L, and a free chlorine content of 20-140 mg/L, wherein said free chlorine content comprises ≥90 w/w % hypochlorous acid (HClO), ≤10 w/w % chlorine (Cl$_2$), and ≤3 w/w % hypochlorite (ClO$^-$).

In a fourth principal embodiment the invention provides a method of treating Buruli ulcers caused by *Mycobacterium ulcerans* in a patient in need thereof comprising topically applying to said ulcers a therapeutically effective amount of a hypotonic, acid oxidizing, aqueous solution comprising a pH of from 2.5 to 6, a chloride content of less than 400 mg/L, and a free chlorine content of 20-140 mg/L, wherein said free chlorine content comprises ≥90 w/w % hypochlorous acid (HClO), ≤10 w/w % chlorine (Cl$_2$), and ≤3 w/w % hypochlorite (ClO$^-$).

In a fifth principal embodiment the invention provides a method of treating a SARS Cov2 infection in a patient in need thereof comprising topically applying to the nasal passage and/or throat and/or upper respiratory tract of said patient a therapeutically effective amount of a hypotonic, acid oxidizing, aqueous solution comprising a pH of from 2.5 to 6, a chloride content of less than 400 mg/L, and a free chlorine content of 20-140 mg/L. wherein said free chlorine content comprises ≥90 w/w % hypochlorous acid (HClO), ≤10 w/w % chlorine (Cl$_2$), and ≤3 w/w % hypochlorite (ClO$^-$).

Additional advantages of the invention are set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying drawings, which are incorporated in and constitute a part of this specification, illustrate several embodiments of the invention and together with the description serve to explain the principles of the invention.

DETAILED DESCRIPTION

Definitions and Use of Terms

Figure 1:
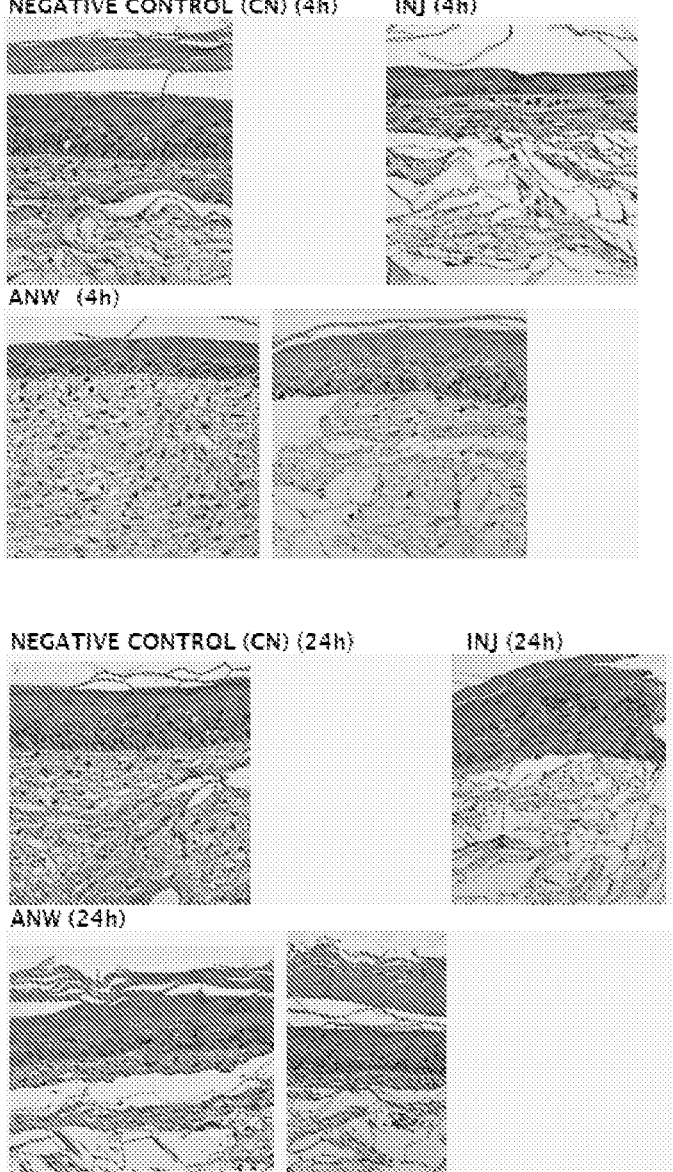
FIG. 1 are histological analyses of injured tissue 4 hours and 24 hours after injury, after application of an active treatment (APR TD011) and a negative control, as described in Example 3.

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

As used in the specification and claims, the singular forms a, an, and the include plural references unless the context clearly dictates otherwise. For example, the term "a specification" refers to one or more specifications for use in the presently disclosed methods and systems. "A hydrocarbon" includes mixtures of two or more such hydrocarbons, and the like. The word "or" or like terms as used herein means any one member of a particular list and also includes any combination of members of that list.

As used in this specification and in the claims which follow, the word "comprise" and variations of the word, such as "comprising" and "comprises," means "including but not limited to," and is not intended to exclude, for example, other additives, components, integers or steps. When an element is described as comprising one or a plurality of components, steps or conditions, it will be understood that the element can also be described as "consisting of" or "consisting essentially of" the component, step or condition, or the plurality of components, steps or conditions.

When ranges are expressed herein by specifying alternative upper and lower limits of the range, it will be understood that the endpoints can be combined in any manner that is mathematically feasible. Thus, for example, a range of from 50 or 80 to 100 or 70 can alternatively be expressed as a series of ranges of from 50 to 100, from 50 to 70, and from 80 to 100. When a series of upper bounds and lower bounds are related using the phase "and" or "or", it will be understood that the upper bounds can be unlimited by the lower bounds or combined with the lower bounds, and vice versa. Thus, for example, a range of greater than 40% and/or less than 80% includes ranges of greater than 40%, less than 80%, and greater than 40% but less than 80%.

When an element of a process or thing is defined by reference to one or more examples, components, properties or characteristics, it will be understood that any one or combination of those components, properties or characteristics can also be used to define the subject matter at issue. This might occur, for example, when specific examples of an element are recited in a claim (as in a Markush grouping), or an element is defined by a plurality of characteristics. Thus, for example, if a claimed system comprises element A defined by elements A1, A2 and A3, in combination with element B defined by elements B1, B2 and B3, the invention will also be understood to cover a system defined by element A without element B, a system in which element A is defined by elements A1 and A2 in combination with element B defined by elements B2 and B3, and all other possible permutations.

"Therapeutically effective amount" means that amount which, when administered to a human for supporting or affecting a metabolic process, or for treating or preventing a disease, is sufficient to cause such treatment or prevention of the disease or supporting or affecting the metabolic process.

When used herein the term "about" will compensate for variability allowed for in the pharmaceutical industry and inherent in products in this industry, such as differences in product strength due to manufacturing variation and time-induced product degradation. The term allows for any variation which in the practice of good manufacturing practices would allow the product being evaluated to be considered therapeutically equivalent or bioequivalent in humans to the recited strength of a claimed product.

In the context of the present invention insofar as it relates to any of the disease conditions recited herein, the term "treatment" means to reduce the occurrence of a symptom or condition, or to relieve or alleviate at least one symptom associated with such condition, or to slow or reverse the progression of such condition, or to manage or affect the metabolic processes underlying such condition. Within the meaning of the present invention, the terms also denote to arrest, delay the onset (i.e., the period prior to clinical manifestation of a disease) and/or reduce the risk of developing or worsening a disease. Whenever a treatment is specified herein, or a particular target of the treatment is given, it will be understood that such treatment yields a clinical meaningful benefit. Thus, for example, when the treatment reduces the bacterial load, or treats a secondary infection, it will be understood that the bacterial load is reduced by a clinically meaningful amount, or the secondary infection is treated to a clinically significant degree.

The phrase "acceptable" as used in connection with compositions of the invention, refers to molecular entities and other ingredients of such compositions that are physiologically tolerable and do not typically produce untoward reactions when administered to a subject (e.g., a mammal such as a human).

When published test methodologies and diagnostic instruments are referred to herein, it will be understood that the test methodology or diagnostic instrument is performed based on the version in effect on Jul. 1, 2019, unless otherwise stated to the contrary herein.

Discussion of Principal Embodiments

The invention can be defined based on several principal embodiments which can be combined among themselves and with any subembodiment in any manner physically and mathematically possible to create additional embodiments. In a first principal embodiment the invention provides a method of treating a wound caused by Epidermolysis Bullosa ("EB") in a patient in need thereof comprising topically applying to said wound a therapeutically effective amount of a hypotonic, acid oxidizing, aqueous solution comprising a pH of from 2.5 to 6, a chloride content of less than 400 mg/L, and a free chlorine content of 20-140 mg/L, wherein said free chlorine content comprises ≥90 w/w % hypochlorous acid (HClO), ≤10 w/w % chlorine (Cl$_2$), and ≤3 w/w % hypochlorite (ClO$^-$).

In a second principal embodiment the invention provides a method of treating an EGFR inhibitor-induced skin toxicity in a patient in need thereof comprising topically applying to skin affected by the skin toxicity a therapeutically effective amount of a hypotonic, acid oxidizing, aqueous solution comprising a pH of from 2.5 to 6, a chloride content of less than 400 mg/L, and a free chlorine content of 20-140 mg/L, wherein said free chlorine content comprises ≥90 w/w % hypochlorous acid (HClO), ≤10 w/w % chlorine (Cl$_2$), and ≤3 w/w % hypochlorite (ClO$^-$).

In a third principal embodiment the invention provides a method of treating a topical disorder caused by Hailey-Hailey disease ("HHD") in a patient in need thereof comprising topically applying to skin affected by said disorder a therapeutically effective amount of a hypotonic, acid oxidizing, aqueous solution comprising a pH of from 2.5 to 6, a chloride content of less than 400 mg/L, and a free chlorine content of 20-140 mg/L, wherein said free chlorine content comprises ≥90 w/w % hypochlorous acid (HClO), ≤10 w/w % chlorine (Cl$_2$), and ≤3 w/w % hypochlorite (ClO$^-$).

In a fourth principal embodiment the invention provides a method of treating Buruli ulcers caused by *Mycobacterium ulcerans* in a patient in need thereof comprising topically applying to said ulcers a therapeutically effective amount of a hypotonic, acid oxidizing, aqueous solution comprising a pH of from 2.5 to 6, a chloride content of less than 400 mg/L, and a free chlorine content of 20-140 mg/L, wherein said free chlorine content comprises ≥90 w/w % hypochlorous acid (HClO), ≤10 w/w % chlorine (Cl$_2$), and ≤3 w/w % hypochlorite (ClO$^-$).

In a fifth principal embodiment the invention provides a method of treating a SARS Cov2 infection in a patient in need thereof comprising topically applying to the nasal passage and/or throat and/or upper respiratory tract of said patient a therapeutically effective amount of a hypotonic, acid oxidizing, aqueous solution comprising a pH of from 2.5 to 6, a chloride content of less than 400 mg/L, and a free chlorine content of 20-140 mg/L. wherein said free chlorine content comprises ≥90 w/w % hypochlorous acid (HClO), ≤10 w/w % chlorine (Cl$_2$), and ≤3 w/w % hypochlorite (ClO$^-$).

Epidermolysis Bullosa ("EB") Subembodiments

The most recent 2008 classification for EB names four categories of EB defined by the level of cleavage at the dermal/epidermal junction. See Fine J D, Eady R A J, Bauer E A, et al. The classification of inherited epidermolysis bullosa (EB): report of the Third International Consensus meeting on Diagnosis and Classification of EB. J Am Acad Dermatol 2008; 58: 931-50. Thus, in one subembodiment, the methods for treating EB are practiced in patients with epidermolysis bullosa simplex (EBS), where blistering occurs in the upper layer of the skin (the epidermis). In another subembodiment, the methods are practiced in patients with dystrophic epidermolysis bullosa (DEB), where blistering occurs below the basement membrane zone in the upper part of the dermis. In still another subembodiment, the methods are practice in patients with junctional epidermolysis bullosa (JEB), where blistering occurs at the junction between the epidermis and the dermis (lower layer of the skin) in a layer of skin known as the basement membrane zone. In yet another subembodiment, the methods are practiced in Kindler Syndrome (KS), an extremely rare recessively inherited disorder in which blistering in infancy is followed by poikloderma and photosensitivity in childhood. (See Burch J M, Fassihi H, Jones C A, Mengshol S C, Fitzpatrick J E, McGrath J A (2006) Kindler syndrome: new mutation and new diagnostic possibilities. Arch Dermatol 142(5):620-4). The blistering can occur at any layer of the skin.

In addition a form of non-genetic EB is also present with similar features. Thus, in yet another subembodiment the methods are practiced in patients with acquired epidermolysis bullosa (EBA), where blistering occurs at the basal derma. It is a chronic autoimmune caused by antibodies targeting type VII collagen, the major component of anchoring fibrils that connect the basement membrane to dermal structures. See Kasperkiewicz M, Sadik C D, Bieber K, Ibrahim S M, Manz R A, Schmidt E, Zillikens D, Ludwig R J. Epidermolysis Bullosa Acquisita: From Pathophysiology to Novel Therapeutic Options. J Invest Dermatol. 2016 January; 136(1):24-33.

According to pheno- and genotype as well as inheritance patterns, the above categories are further classified into various subgroups, some of which contain extremely rare sub entities. Laimer M, Prodinger C, Bauer J W Hereditary Epidermolysis Bullosa. J Dtsch Dermatol Ges. 2015 November; 13 (11): 1125-33. Thus, in further subembodiments:

- the EBS patient has mutations in Keratins 5 and 14; plectin; α6β4 integrin; plakophilin-1; or desmoplakin;
- the JEB patient has mutations in Laminin-332 (laminin 5); type XVII collagen; or α6β4 integrin;
- the DEB patient has mutations in Type VII collagen; or
- the KS patient has a mutation in Kindlin-1.

See Denyer, J., Pillay, E. and Clapham, J. Best practice guidelines for skin and wound care in epidermolysis bullosa. International Consensus. Debra. 2007.

In another subembodiment, in the methods of treating Epidermolysis Bullosa, the wound is selected from the group consisting of skin blisters, mucosal blisters, scalp blistering, scarring alopecia, atrophic scarring, hyperkeratosis, milia, tooth decay, dysphagia, and itchy or painful skin.

In another subembodiment, in the methods of treating Epidermolysis Bullosa, the wound is selected from skin and mucosa blisters and tearing.

In another subembodiment, in the methods of treating Epidermolysis Bullosa, the wound is selected from skin and mucosa blisters and tearing and said treatment comprises a reduction in time required for closure of said wound.

In another subembodiment, in the methods of treating Epidermolysis Bullosa, the wound has a wound bed score (WBS) and said administration reduces said WBS.

In another subembodiment, in the methods of treating Epidermolysis Bullosa, the patient is suffering from an elevation in MMP2 and MMP9 activity and said administration reduces said elevation.

In another subembodiment, in the methods of treating Epidermolysis Bullosa, the method further comprises administering to said patient a topical dressing, aluminum chloride, cyproheptadine, a keratolytic, or a topical softening agent. Any type of dressing commonly used to treat pressure ulcers and other types of wounds could be applied to the area affected by the Epidermolysis Bullosa, following treatment with the solutions of the current invention, including saline gauze, a protease modulating dressing, a collage-nase ointment, a foam dressing, a basic wound contact dressing, and a polyvinylpyrrolidone plus zinc oxide dressing.

In another subembodiment, applicable to the methods of treating EGFR inhibitor-induced skin toxicities, the method further comprises administering to said patient an oral or topical antibiotic or corticosteroid or skin moisturizer. The antibiotic can be administered prophylactically or in response to an active infection.

In still another subembodiment, the method further comprises preventing an infection secondary to the Epidermolysis Bullosa, by administering the solution of the present invention to skin affected by the Epidermolysis Bullosa.

EGFR-Inhibitor Toxicities Subembodiments

Various subembodiments are defined based on the EGFR inhibitor that has caused the toxicity. Thus, in several subembodiments the EGFR inhibitor is selected from the group consisting of tyrosine kinase inhibitors (TKI) (e.g., erlotinib, gefitinib), or monoclonal antibodies (e.g., cetuximab, necitumumab). In other subembodiments the EGFR inhibitor is selected from the group consisting of gefitinib, erlotinib, lapatinib, cetuximab, neratinib, osimertinib, panitumumab, vandetanib, necitumumab, and dacomitinib.

Currently there is no shared international therapeutic protocol for the management of adverse skin events induced by EGFR inhibitors. However, in the Common Terminology Criteria for Adverse Events Guidelines (CTCAE v5.0), in the Multinational Association of Supportive Care in Cancer (MASCC) and in the National Comprehensive Cancer Network (NCCN), several recommendations are exclusively made regarding the pharmacological treatment of injuries skin lesions in acute manifestation.

Thus, in one subembodiment the methods of treating EGFR inhibitor-induced toxicities is practiced in combination with a second treatment selected from the group consisting of topical antiseptics, topical and/or systemic antibiotics (both prophylactically and in response to infection), topical retinoids, and topical and/or systemic steroids. In another subembodiment the patient is suffering from a mild to moderate degree of clinical eczematisation, and the invention is practiced in combination with a tetracycline treatment selected from topical clindamycin 2% or erythromycin 4%, optionally in combination with a topical steroid, or an oral treatment selected from minocycline 100 mg/day or doxycycline 100 mg/day orally. In still another subembodiment the patient is suffering from intense itchy symptoms and the invention is practiced in combination with an antihistamine such as cetirizine.

In another subembodiment, applicable to the methods of treating EGFR inhibitor-induced skin toxicities, the toxicity is selected from the group consisting of xerosis, fissures, pruritus, eczema, skin infections, itching, urticaria, hairgrowth abnormalities, and papulopustular rash, and said application treats one or more of said toxicities.

In another subembodiment, applicable to the methods of treating EGFR inhibitor-induced skin toxicities, the toxicity comprises a wound having a wound bed score (WBS) and said administration reduces said WBS.

In another subembodiment, applicable to the methods of treating EGFR inhibitor-induced skin toxicities, the administration reduces a toxicity grade on a scale selected from the group consisting of NCI-CTCAE v5.0, FACT-EGFRI-18, DIEHL-24, and MESTT.

In another subembodiment, applicable to the methods of treating EGFR inhibitor-induced skin toxicities, the administration improves the quality of life of said patient as measured by EQ-5D-5L/3L for QALYs and/or an additional condition specific questionnaire selected from DLQI (Dermatology Life Quality Index), Skindex-16 or FACT-EGFRI-18.

In another subembodiment, applicable to the methods of treating EGFR inhibitor-induced skin toxicities, the skin toxicity is a target lesion and said treatment reduces the size of said target lesion.

In another subembodiment, applicable to the methods of treating EGFR inhibitor-induced skin toxicities, the method further comprises administering to said patient an oral or topical antibiotic or corticosteroid or skin moisturizer. The antibiotic can be administered prophylactically or in response to an active infection.

In still another subembodiment, the method further comprises preventing an infection secondary to the EGFR-inhibitor induced toxicity, by administering the solution of the present invention to skin affected by the toxicity.

Hailey-Hailey Disease Subembodiments

A diagnosis of Hailey-Hailey disease is made based upon a thorough clinical evaluation, a detailed patient history, identification of characteristic findings and a variety of specialized tests. Thus, in one subembodiment the Hailey-Hailey disease is diagnosed by surgical removal and microscopic examination (biopsy) of affected skin tissue. In one subembodiment biopsied skin reveals abnormal formation of keratin tissue (keratinization) and failure of cell-to-cell adhesion (acantholysis). In another subembodiment the patient has been tested for mutations in the ATP2C1 gene to confirm the diagnosis. In still further subembodiments the Hailey-Hailey patient has secondary bacterial and fungal superinfections that optionally may cause vegetative or malodorous plaques.

In other subembodiments the methods of the present invention are practiced in combination with a therapy selected from cool compresses, dressings, corticosteroid creams, topical antibiotics, and systemic antibiotics. Still further subembodiments are practiced in combination with a therapy for shutting down sweat glands, including botulinum toxin and glycopyrrolate. Further subembodiments are practiced in combination with vitamin A derivatives (retinoids) such as acitretin and etretinate, drugs that suppress the immune system such as alefacept or tacrolimus, and oral magnesium chloride to help the ion pump work better.

In another subembodiment, applicable particularly to Hailey-Hailey Disease, the topical disorder is selected from the group consisting of a skin rash, itching, burning, cracked skin, or secondary infection.

In another subembodiment, applicable particularly to Hailey-Hailey Disease, the topical disorder is a wound selected from skin and mucosa blisters and tearing.

In another subembodiment, applicable particularly to Hailey-Hailey Disease, the topical disorder is a wound selected from skin and mucosa blisters and tearing and said treatment comprises a reduction in time required for wound closure.

In another subembodiment, applicable particularly to Hailey-Hailey Disease, the topical disorder comprises a wound having a wound bed score (WBS) and said administration reduces said WBS.

In another subembodiment, applicable particularly to Hailey-Hailey Disease, the topical disorder comprises relapsing and remitting skin lesions, and said application reduces the length of an outbreak of said lesions or the time between occurrences of said lesions.

In another subembodiment, applicable particularly to Hailey-Hailey Disease, the patient is suffering from a condition selected from loss of functional ATP2C1 keratinocyte activity, oxidative stress in one or more skin lesions, reduced NRF2 activity, or imbalanced TGFβ1 and TGFβ2 expression, reduced proliferation keratinocytes, and said method treats said condition. In another subembodiment, applicable particularly to Hailey-Hailey Disease, the method further comprises administering to said patient a cool compress, a topical dressing, a corticosteroid cream, a topical antibiotic, or a systemic antibiotic (both prophylactically and in response to an active infection).

Any type of dressing commonly used to treat pressure ulcers and other types of wounds could be applied to the area affected by the Hailey-Hailey Disease, following treatment with the solutions of the current invention, including saline gauze, a protease modulating dressing, a collagenase ointment, a foam dressing, a basic wound contact dressing, and a polyvinylpyrrolidone plus zinc oxide dressing.

In still another subembodiment, the method further comprises preventing an infection secondary to the Hailey-Hailey Disease, by administering the solution of the present invention to skin affected by the Hailey-Hailey Disease.

Buruli Ulcers

In another subembodiment, applicable particularly to the treatment of Buruli Ulcers, the Buruli Ulcer is characterized by a wound and said treatment comprises a reduction in time required for wound closure.

In another subembodiment, applicable particularly to the treatment of Buruli Ulcers, the Buruli ulcer is characterized by a wound having a wound bed score (WBS) and said administration reduces said WBS.

In another subembodiment, applicable particularly to the treatment of Buruli Ulcers, the Buruli ulcer is characterized by mycolactone secretion and said administration reduces said secretion.

In another subembodiment, applicable particularly to the treatment of Buruli Ulcers, the Buruli Ulcer is characterized by a bacterial load of *Mycobacterium ulcerans*, and said administration reduces said bacterial load.

In another subembodiment, applicable particularly to the treatment of Buruli Ulcers, the method further comprises administering to said patient rifampicin and one or more antibiotics selected from streptomycin, clarithromycin and moxifloxacin.

Any type of dressing commonly used to treat pressure ulcers and other types of wounds could be applied to the area affected by the Buruli Ulcer, following treatment with the solutions of the current invention, including saline gauze, a protease modulating dressing, a collagenase ointment, a foam dressing, a basic wound contact dressing, and a polyvinylpyrrolidone plus zinc oxide dressing.

In still another subembodiment, the method further comprises preventing an infection secondary to the Buruli Ulcers, by administering the solution of the present invention to skin affected by the Buruli Ulcers.

SARS Cov2 Subembodiments

In another subembodiment, applicable particularly to the treatment of SARS Cov2 infection, the administration reduces the viral load of SARS Cov2 in the nasal and upper respiratory tract.

In another subembodiment, applicable particularly to the treatment of SARS Cov2 infection, the administration reduces the spread of SARS Cov2 to the lower respiratory tract such as the trachea or lungs.

In another subembodiment, applicable particularly to the treatment of SARS Cov2 infection, the said administration protects intranasal olfactory neurons from SARS Cov2 infection and damage.

In another subembodiment, applicable particularly to the treatment of SARS Cov2 infection, the composition is administered as a nasal spray from a spray-type device in a volume of from 100 to 1500 mcl, from 250 to 1000 mcl, from 400 to 750 mcl, or 500 mcl per nostril per administration, which can comprise more than one actuation of the device. In another preferred embodiment, these volumes will be administered at least three times per day to each nostril.

In a particularly preferred embodiment, applicable particularly to the treatment of SARS Cov2 infection, the solution will be dispensed from a spray pump that dispenses from 50 to 1000 mcl per actuation, 75 to 500 mcl per actuation, or 85 to 300 mcl per actuation.

In another preferred embodiment, applicable particularly to the treatment of SARS Cov2 infection, the solution will be administered at least three or four times per day to each nostril.

Additional Subembodiments Applicable to Multiple Methods of the Current Invention In another subembodiment, applicable to all of the methods of the current invention, the patient is suffering from one or more biochemical abnormalities selected from nuclear factor kappa B (NF-kB) signalling, Nrf2 activity, IL-1 activity, granulocyte macrophage colony-stimulating factor (GM-CSF) activity, IL-6 activity, MMP 2, MMP 9, TNF-$\alpha$ activity, KGF expression, TGF$\beta$2 expression, TGF$\beta$1 expression, and siATP2C1 keratinocyte proliferation, and said administration treats one or any combination of said biochemical abnormalities.

In another subembodiment applicable to all of the methods of the current invention the solution is stored in primary packaging an amber glass bottle with or without a spray nozzle affixed to the bottle.

In another subembodiment, applicable to the treatment of Epidermolysis Bullosa, EGFR-inhibitor induced toxicities, Hailey-Hailey Disease, and Buruli Ulcers, the composition is administered to an affected topical surface on the body as a spray at approximately 50-500 mcl, 75-400, 75-150, 150-400 mcl, 100 mcl, or 250 mcl per actuation from a pump-type spray device.

In another subembodiment, applicable to the treatment of Epidermolysis Bullosa, EGFR-inhibitor induced toxicities, Hailey-Hailey Disease, and Buruli Ulcers, the composition is administered to an affected topical surface on the body as a spray at approximately 50-500 mcl, 75-400, 75-150, 150-400 mcl, 100 mcl, or 250 mcl per actuation from a pump-type spray device and allowed to air dry without physical intervention.

For Epidermolysis Bullosa, EGFR-inhibitor induced toxicities, Hailey-Hailey Disease, and Buruli Ulcers, the total quantity of the solution administered per administration will depend on the size of the lesion on the skin and the severity of the lesion. Thus, while not intending to be limited, one could apply 2 or 3 sprays of 100 or 250 mcl for a small wound or 10-20 sprays of 100 or 250 mcl for a larger wound. The solution could be administered 2, 3, or even more times per day depending on the severity of the lesion and the amount of irrigation required.

Drug Product/Formulation

The drug product is a hypotonic, acidic, oxidizing solution containing hypochlorous acid (HClO) obtained through a sodium chloride solution electrolysis process. This process yields a hypotonic solution with peculiar characteristics in terms of (i) pH, (ii) Oxidative Reduction Potential (ORP), (iii) free Chlorine species, (iv) purity of HClO, (v) chloride content and (vi) long term stability properties.

The concentrations of free chlorine species (Chlorine (Cl$_2$), Hypochlorite (ClO$^-$) and Hypochlorous Acid (HClO)) are a function of the pH and total chloride content, and can be manipulated by taking advantage of the following dissociation equilibria of gaseous chlorine in water:

$$Cl_2 + H_2O = Cl^- + H^+ + HClO \text{ with } Ka1 \gg 3 \times 10^{-4}$$

$$HClO = H^+ OCl^- \text{ with } Ka2 \gg 2.9 \times 10^{-8}$$

It is possible to calculate the percentage of the three free chlorine species according to the following formulae:

$$\alpha Cl_2 = [H^+]2[Cl^-]/([H^+]2[Cl^-] + [H^+]Ka1 + Ka1Ka2)$$

$$\alpha HClO = [H^+]Ka1/([H^+]2[Cl^-] + [H^+]Ka1 + Ka1Ka2)$$

$$\alpha ClO^- = Ka1Ka2/([H^+]2[Cl^-] + [H^+]Ka1 + Ka1Ka2)$$

For the results expressed as %, the above expressions must be multiplied by 100. The above ion concentrations ([H+] and [Cl-]) are expressed as molarity.

The free chlorine content can range from 20 to 400 mg/l (ppm), but preferably ranges from 20 to 200 mg/l (ppm) or 20 to 140 mg/l (ppm). A free chlorine range of from 40 to 100 ppm is also preferred because it guarantees the characteristics of the product in terms of pH, ORP, purity of HClO and hypotonicity (low chloride content). The compositions of the present invention will always have an acidic pH, be hypotonic, and contain hypochlorous acid as the dominant free chlorine species. In addition, the compositions can be defined by any of the following characteristics, alone or in combination:

free chlorine content of from 20 to 400 mg/l, from 20 to 200 mg/l, from 20 to 140 mg/l, from 40 to 100 mg/l, from 40 to 70 mg/l, or from 70 to 100 mg/l;

a chloride content of less than 500 mg/l, less than 400 mg/l, less than 300 mg/l, or less than 200 mg/l, and preferably greater than 20 or 50 mg/l;

a ClO$^-$ concentration of less than 5 mg/l, 2 mg/l, 0.5 mg/l, or 0.1 mg/l;

a pH of from 2 to 6, 5, 4, or 3, or from 2.5 to 6, 5, 4, or 3;

an oxidation reduction potential (ORP) of from 850 to 1350 mV or from 1000 to 1300 mV; and/or free chlorine content comprising ≥90 w/w % HClO and ≤10 w/w % Cl$_2$, or ≥95 w/w % HClO, <5 w/w % ClO$^-$, and ≤5 w/w % Cl$_2$.

Thus, in one subembodiment the pharmaceutically acceptable composition is a hypotonic aqueous solution comprising a free chlorine content of greater than 20 mg/l. Alternatively, the free chlorine content can range from 20 mg/l to 400 mg/l, from 20 mg/l to 250 mg/l, or from 20 to 140 mg/l.

In another subembodiment the pharmaceutically acceptable composition is a hypotonic aqueous solution comprising a chloride content of less than 400 mg/l.

In still another subembodiment the pharmaceutically acceptable composition is a hypotonic aqueous solution at a pH of from 2.5 to 6 comprising a chloride content of less than 400 mg/l and a free chlorine content of from 20 to 140 mg/l.

In yet another subembodiment the pharmaceutically acceptable composition is a hypotonic aqueous solution at a pH of from 2.5 to 6 comprising a chloride content of less than 400 mg/l and a free chlorine content of from 20 to 400 mg/l, wherein the free chlorine comprises ≥90 w/w % HClO and ≤10 w/w % Cl$_2$, and an ClO$^-$ concentration of less than 5 w/w %, In still another subembodiment the pharmaceutically acceptable composition is a hypotonic aqueous solution at a pH of from 2.5 to 6 comprising a chloride content of less than 400 mg/l, a free chlorine content of from 20 to 400 mg/l, and an oxidation reduction potential (ORP) of from 850 to 1350 mV, wherein the free chlorine comprises ≥90 w/w % HClO and ≤10 w/w % $Cl_2$, and an $ClO^-$ concentration of less than 5 w/w %.

In another subembodiment the pharmaceutically acceptable composition is a hypotonic aqueous solution comprising: (a) a chloride content less than 200 mg/l; (b) a pH of from 2.5 to 3; (c) an oxidation reduction potential (ORP) of from 1000 to 1300 mV; and (d) a free chlorine content of from 40 to 100 mg/l, comprising ≥95 w/w % HClO, ≤5 w/w % $Cl_2$, and <2 w/w % or 0.5 w/w % $ClO^-$ or 0 w/w % $ClO^-$.

In another subembodiment the pharmaceutically acceptable composition is a hypotonic aqueous solution comprising: a pH of from 2.5 to 4.5, a chloride content ≤300 mg/l, and an oxidation reduction potential (ORP) of from 850 to 1350 mV.

In another subembodiment the pharmaceutically acceptable composition is a hypotonic aqueous solution comprising: (a) a chloride content less than 250 mg/l; (b) a pH of from 2.5 to 4; (c) an oxidation reduction potential (ORP) of from 850 to 1350 mV; and (d) a free chlorine content of from 25 to 120 mg/l, comprising ≥92.5 w/w % HClO, ≤7.5 w/w % $Cl_2$, and <1 w/w % or 0 w/w % $ClO^-$.

In another subembodiment the pharmaceutically acceptable composition is a hypotonic aqueous solution comprising: (a) a chloride content less than 200 mg/l; (b) a pH of from 2.5 to 3; (c) an oxidation reduction potential (ORP) of from 1000 to 1300 mV; and (d) a free chlorine content of from 40 to 100 mg/l, comprising ≥95 w/w % HClO, ≤5 w/w % $Cl_2$, and <0.1 w/w % or 0 w/w % $ClO^-$.

The solution of the present invention is preferably supplied in a spray bottle equipped with a spray pump which dispenses anywhere from 100 to 500 microliters per puff, preferably about 250 microliters/puff. In the method of treatment, the solution is preferably applied two or three times per day.

Thus, in still another subembodiment the pharmaceutically acceptable composition is a hypotonic aqueous solution administered as a spray at approximately 250 microliters per actuation from a pump-type spray device.

Method of Administration/Mode of Action

In one embodiment the solution has a mechanical cleansing function. Thus, in one particular embodiment the methods are carried out administering an effective amount of the solution to the affected skin to flow through the affected skin and remove biologic and inert materials.

It has surprisingly been found that this cleansing occurs without washing the skin in the conventional sense, as by running water over the affected skin, drying the affected skin with a cloth or tissue, or otherwise debriding the affected skin. Rather, without wishing to be bound by any theory, it is believed that the solution acts in concert with the skin to urge biological and inert materials to the surface of the skin, where they can no longer interfere with healing process beneath the skin's surface.

Thus, in some embodiments it is important to retain the solution on the skin so that the solution is able to moisten the skin for a period of time sufficient to promote healing and rejuvenation. Thus, in still another embodiment, the methods of the invention further comprise retaining on the skin a moist layer of the solution for a period of time effective to sustain and promote physiological healing. In other embodiments, the administration forms a moist layer of the solution on the affected skin, further comprising allowing the solution to evaporate under ambient conditions without mechanical intervention.

In another subembodiment the composition is administered to an affected topical surface on the body as a spray at approximately 150-400 mcl, 200 to 300 mcl, or 250 mcl per actuation from a pump-type spray device.

In still another subembodiment the composition is administered to an affected topical surface on the body as a spray at approximately 150-400 mcl, 200 to 300 mcl, or 250 mcl per actuation from a pump-type spray device, and allowed to air dry without physical intervention.

In another subembodiment the composition is administered to an affected topical surface on the body as a spray at approximately 150-400 mcl, 200 to 300 mcl, or 250 mcl per actuation from a pump-type spray device, and allowed to air dry without physical intervention followed by topical administration of a secondary treatment.

In yet another subembodiment the composition is administered as a nasal spray from a spray-type device in a volume of from 100 to 1000 mcl per administration, which can comprise more than one actuation of the device.

In another embodiment the methods of the present invention comprising topically administering the solution to profusely cover the affected skin, allowing the solution to dry, and repeating the administration. In a preferred embodiment the methods of the present invention are repeated one or twice per day.

In still another embodiment the methods of the current invention further comprise topically applying to the affected skin a moisturizing cream, lotion, gel or ointment.

EXAMPLES

In the following examples, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention.

Example 1. Description of HClO Solutions of the Present Invention

The Product is a hypotonic, acidic oxidizing solution containing Hypochlorous Acid (HClO) obtained through a Sodium Chloride solution electrolysis process. This process yields a hypotonic solution defined in terms of (i) pH, (ii) Oxidative Reduction Potential (ORP), (iii) free chlorine species and (iv) purity of HClO having long term stability properties. Methods for producing the Product are described in WO/2008/131936 and WO/2007/048772, the disclosure of which are hereby incorporated by reference.

Specifications for hypotonic, acidic oxidizing solution containing Hypochlorous Acid (HClO) are given below in TABLE 1:

TABLE 1

| Property | Specification |
| --- | --- |
| Tonicity | Hypotonic (Chloride content less than 200 mg/l) |
| pH | 2.50-3.00 |
| Oxidation Reduction Potential (ORP) | 1000-1300 mV |

TABLE 1-continued

| Property | Specification |
|---|---|
| Free chlorine* content | 40-100 mg/l |
| Free chlorine species | HClO is not less than 95% of Free Chlorine, ClO⁻ is 0%, $Cl_2$ is less than 5% |

*The Free Chlorine species are Chlorine ($Cl_2$). Hypochlorite (ClO⁻) and Hypochlorous Acid (HClO).

TABLE 2 gives the test results for particular batches meeting the specifications set forth in TABLE 1.

TABLE 2

| Batch | | Specification range | Batch 1 APR TD011 (about 40 ppm of Free Chlorine) | Batch 2 APR TD011 (about 70 ppm of Free Chlorine | Batch 3 APR TD011 (about 100 ppm of Free Chlorine |
|---|---|---|---|---|---|
| pH | | 2.5-3.0 | 2.76 | 2.77 | 2.62 |
| ORP (mV) | | 1000-1300 | 1121 | 1153 | 1144 |
| Free chlorine content (ppm) | | 40.0-100.0 | 45.8 | 67.5 | 97.8 |
| Free chlorine species | % HClO | >95% | 97.00 | 98.17 | 96.91 |
| | % ClO⁻ | Absent | 0.00 | 0.00 | 0.00 |
| | % $Cl_2$ | <5% | 3.00 | 1.83 | 3.09 |
| Chloride content (ppm) | | <200 | 189.5 | 116.8 | 141.3 |

The hypotonic, acidic oxidizing solution containing Hypochlorous Acid (HClO) is provided in an amber glass bottle and can be equipped with a spray pump which dispenses approximately 100 or 250 μl/puff. ICH (International Conference on Harmonization). Stability has been performed on several batches and, based on the data generated, the assigned shelf life is 24 months if stored between 5° C. and 25° C.

Example 2. Instructions for Use

Suitable instructions for using the solutions of the current invention, including the product of Example 1, are given below:

Mechanism of Action

The moist layer left on the lesion after administration accounts for the creation of an ideal microenvironment to sustain the physiological healing process thanks to three features of the solution (highly pure HClO, pH<3.0, and ORP>1000 mV).

The solution contains hypochlorous acid (HClO), which acts as an antimicrobial agent and a preservative by inhibiting the growth of microorganisms within the solution, and preventing contamination by exerting a local ancillary antimicrobial effect on the lesion surface.

HClO, characterized by a neutral charge, penetrates the negatively charged bacterial membrane very efficiently where it exerts its antimicrobial action.

pH<3.0 affects bacterial growth by creating an environment unfavorable to bacterial growth. Furthermore, the acid environment promotes tissue oxygenation by the Bohr effect, and inhibiting the penetration of healthy cells by ammonia by-products of bacteria catabolism.

The high ORP physically damages the cellular membrane of micro-organisms, inactivating their defense mechanisms.

The combination of low pH and high ORP has a role in the inhibition of matrix metalloproteases (MMPs). Elevated MMPs activity causes delayed wound healing through degradation of collagen matrixes vital to the healing process. The inhibition of MMP activity may contribute to restart the physiological healing process.

Directions for Use

Apply the solution at the onset of manifestations. The solution is ready for use with no mixing or dilution required.

Apply the solution directly on the affected area:

Open the bottle by unscrewing the cap

Open the plastic sachet containing the spraying cap by cutting the upper side

Extract the spraying cap from the sachet, by taking it out from the cap, paying attention not to touch the straw Insert the straw into the bottle Screw the spraying cap on the bottle neck Before using the product for the first time, spray into air to start the pump, until a nebulized solution is seen Apply the solution directly on the injured zone, by spraying it, in order to profusely cover the affected area, let it dry, repeat the application Apply the treatment once or twice a day Do not unscrew the spraying cap after its installation; do not apply again the screw cap to the bottle after the installation of the spraying cap Close with the overcap just after use Use the device within 30 days after the first opening For the treatment administration, if the patient is going to use make up or another topical dressing, he/she should do so only after the product is dried for at least two minutes after its application. If the patient has to shave, he/she should do so before the application of the product.

Example 3. Evaluation of Anti-Inflammatory and Tissue Regeneration Properties, with Particular Application to Epidermolysis Bullosa The role of hypotonic, acidic oxidizing solution containing Hypochlorous Acid (HClO) (named in this indication as APR TD-011) meeting the specifications in Example 1 has been assessed in an in vitro wound healing model on FT-SKIN to define its mechanism of action and to assess its tissue regeneration properties at epidermal and dermal levels after 4 hours and 24 hours of treatment post-injury with a transcriptional study (qRT-PCR).

Methods:

Test System:

An experimental in vitro model of wound healing has been developed on a "Full-thickness skin model" (FT-skin) by inducing a reproducible mechanical injury that involves both the epidermal and the dermal compartment, mimicking the different phases of the healing process.

The Phenion® Full Thickness Skin Model is produced by Henkel (Dusseldorf, Germany, diameter 1.3 cm). In this model, epidermal keratinocytes and dermal fibroblasts (derived from biopsy material from healthy donors) form a multi-layered skin that resembles human skin under culture conditions. Briefly, fibroblasts are grown in a specialized stable matrix that does not contract under fibroblast traction forces. After the development of this dermal equivalent, keratinocytes are overlaid and within a few days they develop an epidermis with clearly recognizable layers. Both the epidermis and dermis form a physiologically functional unit and, like human skin, the epidermis produces various markers of differentiation (cytokeratin 10, filaggrin, transglutaminase and involucrin). The epidermal-dermal junction is characterized by basal membrane proteins (laminin and collagen IV). In the dermal compartment, de novo synthesis of elastin and fibronectin has been demonstrated. The proliferative cells of the basal layer are identified by Ki-67 staining. The model is fully developed after a cultivation period of 5 weeks.

The injury in this experiment was simulated with a biopsy punch 2 mm in diameter. Four symmetric injuries have been induced reaching both dermal and epidermal compartments.

Test products were applied to each wound for a total volume of 50 μL.

Real Time PCR:

RNA Extraction, cDNA Retrotranscription and REAL TIME PCR:

A rapid, phenol-free, filter-based RNA isolation system was used to extract the total RNA from cellular samples. A high capacity cDNA reverse transcription kit was used to synthetize cDNA from RNA. The instrument Applied Biosystems 7500 Fast Real Time PCR with fluorescent-based PCR chemistry, implementing the TaqMan assay, was used to study gene expression of significant biomarkers.

Gene expression is the process by which the inheritable information in a gene, such as the DNA sequence, is made into a functional gene product, such as protein or RNA. Relative quantification determines the change in the expression of a nucleic acid sequence in a test sample relative to the same sequence in a calibrator sample. GAPDH was used as an endogenous control gene to normalize input amounts.

Each replicate was assessed in triplicate. At the 2× TaqMan Fast Universal PCR Master Mix was added Taqman gene expression assay and cDNA (25 ng) for a total volume of 20 μL. The Thermal condition steps in the ABI PRISM 7500 Fast are: 95° C. 20 sec; 40 cycles (95° C. 3 sec+60° C. 30 sec).

The following genes were analyzed:

At 4 h: NRF-2, HO-1, GPX, GSR, GST, KGF, TGFβ2, TGFβ3, Nf-kb, VEGF-C, PDGF

At 24 h: IL-1α, TNF-α, Nf-kB, Nrf2, KGF eTGFβ2 eβ3, VEGF-C, PDGF

The early time point enables an evaluation of the antioxidant mechanism of action of the products together with the early inflammatory phase. The 24 h time point enables an evaluation of the late inflammatory phase of wound healing with the overlapping re-epithelialization, proliferative phase, taking into account the first sign of tissue recovery inducing the expression of growth factors involved in vascular proliferation and stabilization.

Product efficacy is compared to the injured tissue to evaluate a restoration of the injured situation. Orange boxes correspond to a significant overexpression of the genes while the green boxes correspond to a significant downregulation of the gene expression with respect to both negative control (CN) (not injured and not treated) and injured but not treated (INJ). The comparison is charted in the two columns in TABLE 3. In particular, TABLE 3 reports real time PCR results of APR TD011 (injured and treated with APR TD011). All the genes were analyzed after 4 h and 24 h after injury.

A) Calibrator sample for all samples is the negative control (untreated and not injured tissue (CN)).

B) Calibrator sample for all samples is the injured control (injured and not treated (INJ)).

TABLE 3

| Not Injured control (CN) | | Injured Control (INJ) | |
|---|---|---|---|
| 4 H | APR TD011 | 4 H | APR TD011 |

TABLE 3-continued

| Not Injured control (CN) | | Injured Control (INJ) | |
|---|---|---|---|
| GPX1 | 1.217 | GPX1 | 1.040 |
| GSR | 0.910 | GSR | 1.402 |
| GSTA1 | 0.906 | GSTA1 | 2.232 |
| HMOX1 | 1.257 | HMOX1 | 1.115 |
| KGF | 4.344 | KGF | 2.493 |
| NFkB | 2.066 | NFkB | 0.980 |
| NRF2 | 1.876* | NRF2 | 1.098 |
| PDGF | 1.262 | PDGF | 1.379 |
| TGFB2 | 2.714 | TGFB2 | 0.917 |
| TGFB3 | 1.576 | TGFB3 | 0.867 |
| VEGF | 1.886* | VEGF | 0.979 |
| 24 H | ANW | 24 H | ANW |
| IL1 α | 1.713 | IL1 α | 0.639* |
| KGF | 3.918 | KGF | 2.774 |
| NFkB | 1.434 | NFkB | 0.770 |
| NRF2 | 0.975 | NRF2 | 0.887 |
| PDGF | 1.700 | PDGF | 1.048 |
| TGFB2 | 1.959* | TGFB2 | 0.716* |
| TGFB3 | 1.492 | TGFB3 | 1.004 |
| TNF α | 1.446 | TNF α | 0.742* |
| VEGF | 1.816* | VEGF | 0.725 |

RQ > 2 significant overexpression (orange); RQ < 0.5 significant downregulation (green) vs CN or INJ; * approaches statistical significance.

Discussion of Results

Anti-Inflammatory Properties

On the basis of the results obtained it is possible to conclude that, at a molecular level, APR TD011 modulates the inflammatory response after 24 hours, based on the low expression of NF-kB and the significant downregulation of IL-1 and TNF-α.

At 4 hours APR TD011 demonstrated GSR and GSTA1 increases relative to the injured control, and an NRF2 increase relative to the negative control, supporting the conclusion that APR TD011 modulates the inflammatory tissue response in a physiological way without involving TGFβ-2 signaling known to shift tissue response to keloid scars.

A lower expression of NF-kB and significant down regulation of IL-1α, TNF-α (compared to injured tissue) confirmed an anti-inflammatory activity of APR TD011, potentially good on skin wounds of EB patients.

Tissue Regeneration Properties

The three isoforms of TGFβ that are present in mammals show a similar biological activity in most in vitro assays. However, there are differences in their in vivo potencies and some biological activities. The relative balance among TGFβ-1, TGFβ-2, and TGFβ-3 determine the outcome of the wound healing process: TGFβ-1 and TGFβ-2 are implicated in cutaneous scarring (fibrotic repair response) and TGF β-3 in prevention of scarring (regenerative response).

TGF β-3 is the most abundant TGFβ isoform in hyperproliferative epithelium and might therefore play an important role in keratinocyte proliferation and differentiation. It is important to underline that, under acidic conditions (pH<3.8), the protein is probably not aggregated: this monomeric form is able alone to accelerate the wounding and could be used in the prevention and/or treatment of fibrotic disorders.

On the basis of the below-described results it is possible to conclude that, at the molecular level, APR TD011 has a positive influence on tissue regeneration in EB after 4 hours and 24 hours because:

(1) Significantly increased expression of KGF both at 4 hours and 24 hours. KGF is known to play an important role in epidermal wound healing. Its production by fibroblasts is upregulated by the presence of interleukin-1. The proliferation of keratinocytes is upregulated by the presence of KGF. A higher increase of KGF induces a development of a thicker neoepidermis.

(2) Lower TGFβ-2 expression at 24 hours compared to the injured control reducing the risk of keloid scars (TGFβ-2 signalling is known to shift tissue response to keloid scars).

(3) Monomeric forms of TGF-β3 are able to promote epithelial regeneration at sites of epithelial damage increasing KGF gene expression (compared to negative control) revealing a re-epithelialization action.

TGF-β3 exists predominantly in two major forms:
monomers in solution at low pH; and
large precipitating aggregates at physiological pH
Aggregation was pronounced in the pH range of 4.3<pH<9.8 with a maximum between pH 6.5 and 8.5. Under the acidic conditions induced by APR TD011 (pH<3.8), the protein was not aggregated. APR TD011 with its low pH seems to maintain a monomeric form of TGF-β3 that can be useful for acceleration of wound healing and/or the inhibition of scarring, in the promotion of epithelial regeneration, and in the prevention and/or treatment of fibrotic disorders.

As shown in FIG. 1 and discussed in TABLE 4 below, histological analyses of the tissue after 4 hours and 24 hours confirmed optimal tissue regeneration properties of APR TD011 ("ANW"). After 4 hours APR TD011 treatment, the tissue morphology appeared significantly well conserved compared to the injured tissue with a well conserved matrix integrity and a lower number of dead cells, suggesting an early protection/recovery of tissue integrity.

process had begun), and reduction in pruritus, all valuable aspects from a patient perspective.

Figure 2:
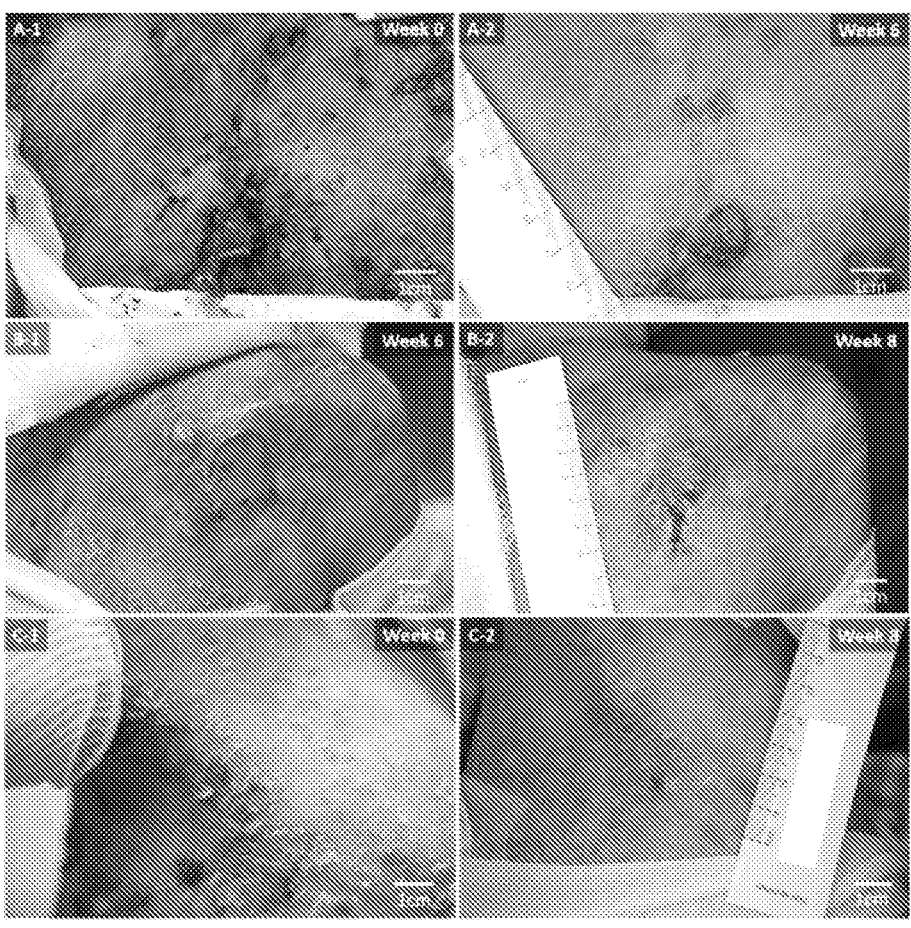
FIG. 2 is a series of photographs depicting results in a 24-year old patient with severe generalized Recessive Dystrophic Epidermolysis Bullosa treated according to the methods of the present invention, as described in Example 3.

FIG. 2 depicts treatment results in a 24-year old patient with severe generalized RDEB. FIG. 2(A) is a comparison of a thoracic wound at week 0 (A-1; perilesional inflammation and scaling, crusts, exudate) and week 6 (A-2; wound cleaner, smaller and more superficial with minimal perilesional inflammation signs). FIG. 2(B) is a picture of the wound on the right scapula showing a reduction in size within 2 weeks and less perilesional scaling. FIG. 2(C) shows inflammatory signs in the left axilla including redness, crusts, and scales ameliorated between week 0 (C-1) and week 8 (C-2).

Figure 3:
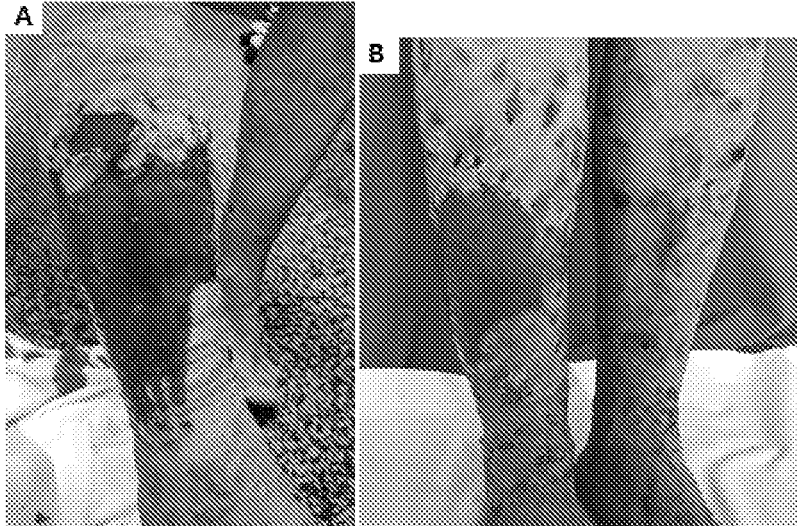
FIG. 3 is pair of photographs of the lower leg of two-year-old chronic wound of a Junctional Epidermolysis Bullosa patient treated according to the methods of the present invention, as described in Example 3.

FIG. 3 is a photograph of the lower leg of two-year-old chronic wound of a JEB patient treated with the product. Photo 3(A) shows the wound still unsolved after several different treatments. Photo 3(B) shows a strong improvement of the wound after 4 weeks of treatment.

Example 4. Evaluation of Product and its Ability to Treat EGFR Inhibitor-Induced Skin Toxicities The role of hypotonic acid oxidizing water containing Hypochlorous acid (HClO) (named in this indication as APR TM-011) meeting the specification reported in example 1 has been assessed in a clinical trial in patients under Cetuximab treatment.
Methods:

An evidence was collected among patients on a cetuximab-based regimen. Each patient underwent 3 outpatient visits within 3 months, organized as follows:

TABLE 4

| PRODUCTS | STRATUM CORNEUM and EPIDERMIS | DERMIS & DEJ |
|---|---|---|
| | 4 h and 24 h | |
| CONTROL | The standard morphology epidermis is observed with regular staining and thickness. | The dermis layer is composed of dermal fibroblastsm, embedded in a recognizable biomatrix consisting of tissue-typical matrix proteins. A functional basal membrane consisting of matrix proteins is developed and visible near the papillar dermis |
| INJURED (near the injury) | At injury level the SC integrity is lost and several necrotic keratinocytes are visible | Severe modification and damages to dermal matrix integrity; fibroblasts are visible in the detached matrix. |
| | 4 h | |
| ANW | The standard morphology epidermis is observed with regular staining and thickness. | The dermis layer presented more fibroblasts than the control tissue in the upper and intermediate dermis, embedded in a recognizable biomatrix consisting of tissue-typical matrix proteins. |
| | 24 h | |
| ANW | The standard morphology epidermis is observed with regular staining and thickness. | Less dense matrix with conserved papillar region with visible fibroblasts. Modification to dermal matrix integrity due to 24 h exposure of skin to acid pH |

Two patients with EB, and open lesions in the skin from the EB, were treated with the solution described in Example 1. The patients were instructed to apply the solution according to Example 2. After a few weeks of treatment, each of the patients reported improvements as shown by a reduction of chronic wound size, improvement of perilesional inflammatory signs (an indication that the physiological healing initial visit intermediate visit final visit.

The intermediate visit was scheduled from the initial and final visit at a distance of 15/30 days depending on the patient's health conditions. An evaluation form was filled in by the clinician at the time of the first visit and updated on the two subsequent visits. At the time of the first visit to the patient, a daily treatment was indicated according to the following treatment scheme:

morning: hydration with base cream noon: dispensing puffs of hypotonic acid solution containing hypochlorous acid on the face, chest and back evening: hydration with base cream A clinician evaluation form was structured in 9 items focused on: previous treatment, treatment with hypotonic acid solution containing hypochlorous acid, home treatment, adjuvant treatment, type of wound, evaluation of the lesion (width and length in centimeters), perilesional skin, evaluation of the quality of life and suspension of the evaluation.

The clinical appearance of the perilesional skin was investigated by the state of erythema, maceration, xerosis, burning, itching and inflammation of which the severity level was indicated: mild, moderate or severe. The characteristics and evolution of the wound bed were detected by the modified Wound Bed Score (WBS). The parameters examined were: active edge, black eschar, granulation depth/tissue, exudate quantity, edema quantity, perilesional skin, skin toxicities/eczema, callosity/fibrosis, rosy wound bed, ulcer duration before the current treatment. Each parameter was assigned a score that could range from 0 to 2. The sum of all the scores defines the total score, which may take a value between 0 (minimum or worst score) and 18 (maximum or best score).

Quality of life was assessed through the QoL-EQ 5D. The general areas of health status investigated were: mobility, personal care, usual activities, discomfort/pain, anxiety and depression. The condition of each of the aforementioned areas could be characterized by one of the following states: no problem, some problem or significant problem.

Finally, the perception of the patient's current state was measured using a numerical scale characterized by a range of values ranging from 0 (equal to a poor state of health) to 100 (better health). The safety of the treatment was evaluated based on the presence or absence of manifestations such as: intolerance, wound infection or adverse event. The response method was: multiple choice answer for 7 items and open for 2 items.

Results:

The observation was carried out on 15 patients, consisting of 10 men and 5 women with an average age of 60 years, who, after the first chemotherapy treatment, showed acneiform cetuximab lesions.

The lesions were located on the chest, arms, and face. At the beginning of treatment:

LESION ASSESSMENT—The lesions measured had different sizes. The width and length were measured in centimeters. In the 15 patients the widths measured ranged from 5 cm to 22 cm, while the lengths ranged from 10 cm to 40 cm. The patient with the smallest injured area had a lesion 5 cm×10 cm in size, while the patient with the largest injured area had a 22 cm×40 cm lesion.

PERILESIONAL SKIN—The perilesional skin of all patients showed itching and inflammation predominantly. The pruritus was moderate for 60% of patients and mild for 40%. Moderate inflammation was present in 60% of the patients; mild inflammation was present in 40%. In 6.7% of patients the skin showed slight burning.

WBS SCORE (modified)—In 40% of patients the total WBS Score was equal to 14; in 33.3% of patients the total WBS score was 15; and in 26.7% of patients the total WBS score was 16.

QUALITY OF LIFE—Quality of life was assessed using the QoL-EQ 5D. Significant problems were discomfort/pain in 46.7% of patients while 33.3% of patients expressed difficulty in carrying out usual activities.

All patients reported suffering from some anxiety and depression. 86.7% manifested some difficulty in personal care, 46.7% in usual activities and 20% experienced a state of discomfort and pain.

None of the patients experienced mobility problems. Furthermore, no problem of discomfort and pain was declared in 33.3% of patients, from 20% in usual activities and from 13.3% in personal care.

Out of a total of 100, the evaluation of today's expressed status was 40 for 20% of patients, 50 and 60 respectively for 40% of them.

At the end of treatment:

LESION ASSESSMENT—In all patients a reduction in the area of the lesions was detected: 93.3% of patients had a greater than 90% reduction in the area while 1 patient had a reduction of 88.9% (TABLE 5).

PERILESIONAL SKIN—No patient reported pathological manifestations of symptoms on perilesional skin.

WBS SCORE (modified)—The WBS score in all patients was 18. (TABLE 6)

QUALITY OF LIFE—All patients reported that they do not suffer from any problems except for anxiety and depression. (TABLE 7)

For all patients the evaluation of today's status at the end of treatment was 80. Furthermore, all patients were able to complete the treatment based on hypotonic acid solution containing hypochlorous acid without at any time experiencing phenomena of intolerance.

TABLE 5

| | | | | | | | % reduction of the lesion Area at the end of treatment − area at the beginning of treatment/area at |
| | Start of Treatment | | | End of Treatment | | | |
| PATIENT | width (cm) | length (cm) | Area (cm²) | width (cm) | length (cm) | Area (cm²) | the beginning of treatment*100 |
|---|---|---|---|---|---|---|---|
| 1 | 20 | 30 | 600 | 5 | 5 | 25 | −95.83 |
| 2 | 20 | 40 | 800 | 5 | 10 | 50 | −93.75 |
| 3 | 6 | 10 | 60 | 1 | 2 | 2 | −96.67 |
| 4 | 21 | 37 | 777 | 6 | 9 | 54 | −93.05 |

TABLE 5-continued

| | Lesion Assessment | | | | | | |
|---|---|---|---|---|---|---|---|
| | Start of Treatment | | | End of Treatment | | | % reduction of the lesion Area at the end of treatment − area at the beginning of treatment/area at |
| PATIENT | width (cm) | length (cm) | Area (cm$^2$) | width (cm) | length (cm) | Area (cm$^2$) | the beginning of treatment*100 |
| 5 | 15 | 30 | 450 | 5 | 10 | 50 | −88.89 |
| 5 | 21 | 32 | 672 | 6 | 7 | 42 | −93.75 |
| 6 | 5 | 10 | 50 | 2 | 2 | 4 | −92.00 |
| 7 | 18 | 25 | 450 | 4 | 6 | 24 | −94.67 |
| 8 | 22 | 40 | 880 | 5 | 11 | 55 | −93.75 |
| 9 | 20 | 30 | 600 | 4 | 7 | 28 | −95.33 |
| 10 | 6 | 10 | 60 | 1 | 2 | 2 | −96.67 |
| 11 | 20 | 38 | 760 | 5 | 10 | 50 | −93.42 |
| 12 | 15 | 25 | 375 | 5 | 5 | 25 | −93.33 |
| 13 | 15 | 30 | 450 | 5 | 5 | 25 | −94.44 |
| 14 | 20 | 25 | 500 | 5 | 8 | 40 | −92.00 |
| 15 | 22 | 30 | 660 | 4 | 5 | 20 | −96.97 |

TABLE 6

| | WBS Score | |
|---|---|---|
| | WBS SCORE | |
| PATIENT | Start of treatment | End of treatment |
| 1 | 14 | 18 |
| 2 | 15 | 18 |
| 3 | 16 | 18 |
| 4 | 16 | 18 |
| 5 | 14 | 18 |
| 6 | 14 | 18 |
| 7 | 14 | 18 |
| 8 | 15 | 18 |
| 9 | 16 | 18 |
| 10 | 14 | 18 |
| 11 | 15 | 18 |
| 12 | 15 | 18 |
| 13 | 15 | 18 |
| 14 | 14 | 18 |
| 15 | 16 | 18 |

TABLE 7

| | Quality of Life | | | | | |
|---|---|---|---|---|---|---|
| | Start of treatment | | | End of treatment | | |
| QoL-EQ 5D | NP N (%) | QP N (%) | RP N (%) | NP N (%) | QP N (%) | RP N (%) |
| Mobility | 15 (100) | | | 15 (100) | | |
| Personal Care | 2 (13.3) | 13 (86.7) | | 15 (100) | | |
| Usual Activities | 3 (20) | 7 (46.7) | 5 (33.3) | 15 (100) | | |
| Discomfort/Pain | 5 (33.3) | 3 (20) | 7 (46.7) | 15 (100) | | |
| Anxiety/Depression | | 15 (100) | | | 15 (100) | |

NP: ZERO PROBLEM; QP: SOME PROBLEM; RP: RELEVANT PROBLEM.

Conclusions:

The application of the hypotonic oxidizing acid solution containing hypochlorous acid to cetuximab skin lesions improves the patient's response to chemotherapy treatment. The lesions undergo a progressive improvement not only in dimension but also in the characteristics and in the correlated symptomatology: the lesion remains circumscribed and undergoes a reduction in size; the perilesional skin remains intact and it also reduces the events of itching and inflammation.

It is also evident that, beyond anxiety and depression related to the main condition of the disease, the control and tolerability of the skin situation, which does not aggravate the perception of one's own body image, translates into a better quality of life on a social level. At the end of the treatment, the parameters indicating "today's state of health" stood at 80/100 for all patients. The good results obtained are confirmation of the fact that the product should be used at the first onset of cutaneous manifestations that normally appear at the first, second cycle of anticancer therapy.

Example 5. Evaluation of Antioxidant and Tissue Regeneration Properties with Particular Application to Hailey-Hailey Disease The role of hypotonic acid oxidizing water containing Hypochlorous acid (HClO) (named in this indication as APR TD-012) meeting the specification reported in example 1 has been assessed in an in vitro model in order to gain a better understanding of the molecular pathway modulated by APR TD012 in HHD: a HaCaT keratinocyte-derived cell line has been transfected with small interfering RNAs (siRNAs) validated for human ATP2C1 to obtain knockdown of the gene expression as occurs in HHD patients (named siATP2C1 cells).

Methods:

Cell Culture:

A HaCaT keratinocyte-derived cell line was grown in DMEM medium with 10% Fetal Bovine Serum (FBS), 5% L-Glutamine, 2% penicillin and streptomycin, at 37° C. with 5% CO2.

Cell Culture and Transfection:

HaCaT cells (70-80% confluent) were maintained in modified low calcium medium and transfected using the Lipofectamine RNAiMAX transfection Reagent according to manufacturer's instructions (Thermo Fisher Scientific, MA USA) with 100 nmol $L^{-1}$ small interfering RNAs (siRNAs) for validated human ATP2C1 (L-006119-00; Thermo Scientific/Dharmacon, Lafayette, CO, U.S.A.) and corresponding control scrambled siRNAs.

Cell Viability Assay:

HaCaT cells (siCTR and siATP2C1) were cultured in a collagen-treated dish and used for $[^{3H}]$thymidine assay at the second passage. Cells were transfected for 24 h with 100 nm of either siATP2C1 or si-CTR (Ambion) by means of RNAiMAX reagent (Invitrogen) and treated with 100 μM APR-TD012. As control samples, cells were treated with equal volumes of the vehicle (H2O). Cell viabilities were assayed by using the MTS-based assay CellTiter 96® AQueous One Solution Cell Proliferation Assay (G3580; Promega, Madison, WI, USA). Absorbances were measured at 490 nm by using GloMax Multidetection System (Promega). Measurements were performed in technical triplicates and figures show the averages±SEM of at least 2 biological replicates.

Western Blot Assay:

Cells were lysed in Tris HCl 20 mM pH7.5, NaCl 150 mM, EDTA 1 mM pH 8, Triton 1%, NaF 30 mM, Na3VO4 1 mM, PMFS 1 mM, and protease inhibitors (Cocktail-Roche); samples were centrifuged at 13000 rpm for 15 min and supernatant was collected. Quantification was performed with Bradford assay (Bio-Rad). Lysates were denatured at 95° C. and separated through SDS-PAGE on 8% acrylamide gel. After transfer to PVDF membrane, proteins were immunoblotted using standard procedures. The following reagents were purchased from Santa Cruz Biotechnology, Santa Cruz, CA, U.S.A.: tubulin. NRF2 (Abcam, Cambridge, UK).

RNA Analysis and Reverse Transcriptase Polymerase Chain Reaction:

Total RNA was isolated from cells, in guanidine isothiocyanate (Trizol reagent, Thermo Fisher Scientific, MA USA)) and further processed by reverse transcriptase polymerase chain reaction (RT-PCR). Each sample was analyzed in triplicated by qRT-PCR and in at least two independent experiments. qRT-PCR was performed at the opportune annealing temperature with the primers indicated below, with SensiFAST SyBr Hi-ROX kit (Bioline, UK) or with specific TaqMan MGB primers/probe using Taqman gene expression assay (Thermo Fisher Scientific, MA USA).

Statistical Analysis:

Each experiment was repeated at least two times independently. All results were expressed as means SD, and P<0.05 was used for significance. One-way ANOVA analysis for independent samples was used to determine statistical significance.

Results:

Treatment of siATP2C1 cells with APR TD012 demonstrates that APR TD012 is able to restore the expression of the transcription factor Nrf2 that plays a key role in response to oxidative stress (Kensler et al., 2007; Moi et al., 1994; Zhang, 2006); APR TD012 is able to modulate cytokines TGF beta 1 and 2 in different ways; and APR TD012 is able to restore proliferation potential of siATP2C1 keratinocytes. Together, these results indicate that APR TD012 can act directly on keratinocytes by reverting some of the defects observed in the siATP2C1 keratinocytes that are a model for the pathology.

Figure 4:
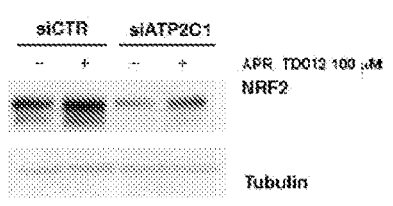
FIG. 4 depicts the effects of a solution of the current invention, illustrating Nrf2 protein expression levels significantly higher in siATP2C1-cells treated with the solution of the present invention than in siATP2C1-cells treated with the vehicle in a model particularly relevant to Hailey-Hailey Disease, as described in Example 5 hereto.
Figure 4:
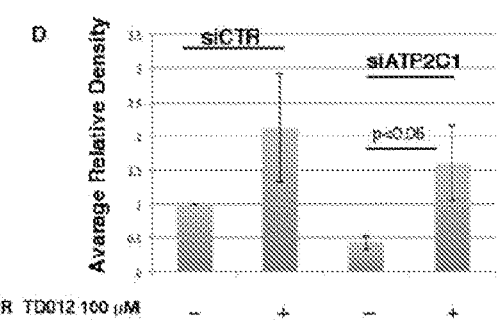
Figure 5:
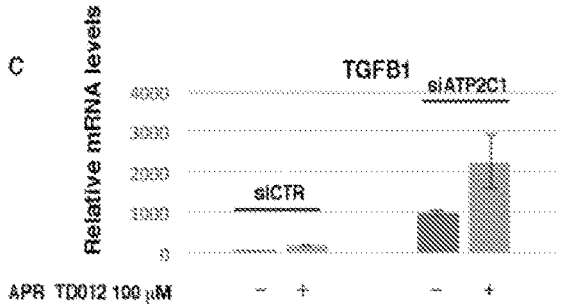
FIG. 5 depicts the effects of a solution of the present invention on TGFB1 and TGFB2 cytokine expression in ATP2C1 defective keratinocytes, in a model particularly relevant to Hailey-Hailey Disease, as described in Example 5 hereto.
Figure 5:
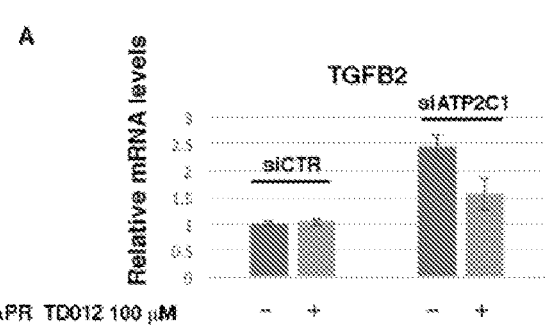

Nrf2 Protein Expression:

It has been previously observed that the expression of NRF2 was decreased in siATP2C1 keratinocytes (Cialfi et al, 2016). This event could play an important role in HHD development since ATP2C1 loss would trigger a mechanism that results in DNA Damage response inhibition. Increased ROS levels as a result of NFR2 down-modulation produce DNA damage up to a threshold that keratinocytes cannot repair, which would then promote lesion manifestation. In this in vitro model, Nrf2 protein expression levels were significantly higher in APR TD012 treated siATP2C1-cells than in siATP2C1-cells treated with the vehicle (FIG. 4). These data suggest that APR TD012 promotes an antioxidant defense response by activating the Nrf2 pathway. HaCaT cells, keratinocyte-derived cell line, was transfected with either siRNA-CTR or siRNA ATP2C1, and 24 hrs later treated with either APR TD012 or $H_2O$ for further 24 hrs. Densitometry analysis of NRF2 expression in HaCaT cells. The averages±standard error of 2 independent experiments are shown.

mRNA Levels of TGFB2 and TGFB1:

HHD lesions are characterized by deregulated cytokine expression and decreased repair properties (Cialfi et al, 2016). The expression levels of the cytokines TGFB1 and TGFB2 that are altered in ATP2C1 defective keratinocytes were analyzed. In the siATP2C1 cells the mRNA levels of TGFB2 and TGFB1 were significantly higher than those of the control siCTR-control cells. FIG. 5 depicts the effects of APR TD012 solution on cytokines in ATP2C1 defective keratinocytes. TGFB-1 and TGFB2 were quantified q-RT-PCR assay. Data are expressed as mean±SD of two independent experiments performed in triplicate.

A significant difference in TGFB1 and TGFB2 levels were observed between the vehicle and APR TD012 treated cells. In particular TGFB1 expression was upregulated in the siATP2C1 cells compared to the siCTR-cells. In APR TD012 treated siATP2C1 cells a significant up-regulation of TGBF1 expression was observed.

The levels of the TGFB2 cytokine were significantly higher in the siATP2C1 treated cells than those of the control cells. A decreased expression of the TGFB2 expression levels was observed in the APR TD012 treated siATP2C1 cells. These data suggest that APR TD012 might influence the pattern of several cytokines in HHD-keratinocytes.

Figure 6:
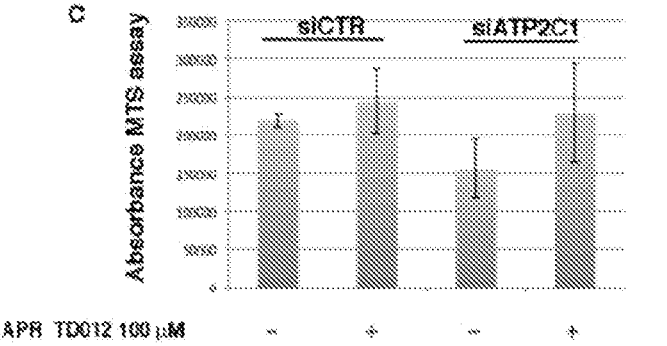
FIG. 6 depicts the effects of treatment of siATP2C1 cells with a solution of the present invention, and the rescue of the defective proliferation of siATP2C1-treated HaCaT cells, as described in Example 5 hereto.

Proliferation of siATP2C1-Treated HaCaT Cells:

It has been already demonstrated that siATP2C1 cells have reduced proliferation compared to siCTR treated cells, confirmed also in this experiment. The treatment of siATP2C1 cells with APR TD012 rescued the defective proliferation of siATP2C1-treated HaCaT cells. FIG. 6 depicts an analysis of proliferative rate of APR TD012 treated cells. HaCaT cells, keratinocyte-derived cell line, was transfected with either siRNA-CTR or siRNAATP2C1, and 24 hrs later treated with either APR TD012 or $H_2O$ for further 24 hrs. Cell number was analyzed by MTS assay after 48 h of transfection. The averages±standard error of 2 independent experiments in triplicate are shown.

Example 6. Testing for Activity Against *Mycobacterium Ulcerans* with Particular Application to Buruli Ulcers The role of hypotonic acid oxidizing water containing Hypochlorous acid (HClO) at two different concentrations (named in this indication as APR TD-013) meeting the specifications reported in example 1 has been assessed in an in vitro model in order to value their activity against *Mycobacterium ulcerans*, the active bacteria involved in the pathogenesis of Buruli ulcers.

Metabolic Activity Testing

In a first step, a resazurin assay was adapted to analyze whether the test solutions (one with 40-70 ppm of free chlorine content named Solution 1 and the second one with 70-100 ppm free chlorine content named Solution 2)) have activity against *M. ulcerans*, which is resistant to many antimicrobial treatments. Cultured bacteria (freshly isolated African reference strain S1013; OD 0.3; log phase) were exposed to the test solutions. 0.1 ml of bacterial culture was mixed with 1.9 ml test solution and incubated for various lengths of time. Mixtures were vortexed immediately and tubes were left to stand for 1 min, 4 min, 9 min, 19 min, or 29 min. After the time elapsed, the bacteria were pelleted by centrifugation (13,300×g for 1 min) and the supernatant was removed. The pellets were immediately resuspended in 0.2 ml 7H9 medium. This suspension was used as inoculum for the resazurin assay.

Figure 7:
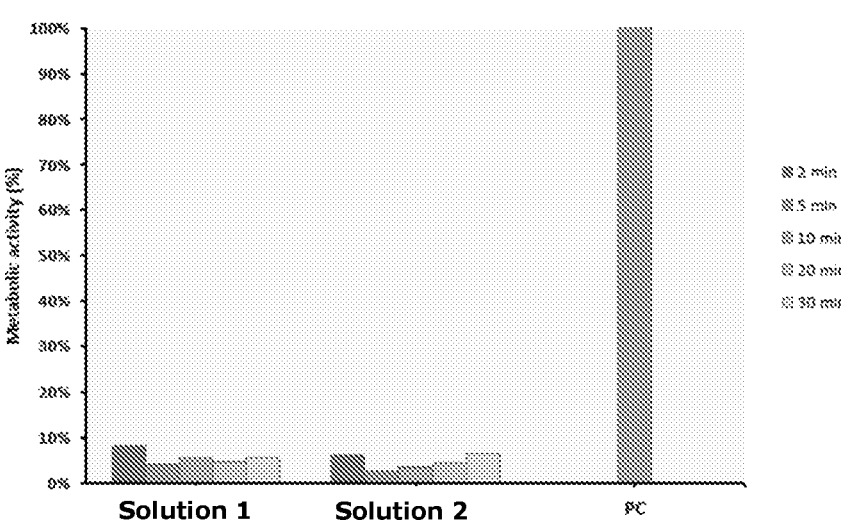
FIG. 7 the calculated metabolic activities of *Mycobacterium ulcerans* bacteria exposed to the solutions of the current invention, as described in Example 6, hereto, with particular application to Buruli Ulcers

For the metabolic activity assay, 20 µl of resazurin was added to the bacterial suspension and incubated for 72 h at 30° C. The fluorescence was measured and metabolic activity was calculated using the included controls. All processes described above were done in duplicates and the results shown below are the mean of both replicates. 2 minutes of exposure with both test solutions resulted in >90% reduction in metabolic activity relative to the untreated control. There was no discernible difference between the activity of the two test solutions on *M. ulcerans* in this assay. The calculated metabolic activities of exposed bacteria are shown in FIG. 7.

Bactericidal Activity Testing

In a next step the bactericidal activity of the Solution 1 and 2 was tested by determining numbers of colony forming units (CFU) in a plating assay. Cultured bacteria (freshly isolated African reference strain S1013; OD 0.3; log phase) were exposed to two test solutions meeting the specifications of Example 1. 0.1 ml of bacterial culture was mixed with 1.9 ml test solution and incubated for 1 min, 4 min, and 9 min. After the elapsed time, the bacteria were pelleted by centrifugation (13,300×g for 1 min) and the supernatant removed. The pellets were immediately resuspended in 0.2 ml 7H9 medium. This suspension was used as inoculum for the determination of CFU counts in duplicates. Ten-fold serial dilutions of each suspension were prepared (from $10^{-1}$ to $10^{-3}$) in 7H9 medium. Each dilution was plated out on 7H9 agar plates (100 µl per plate). All plates were sealed and incubated at 30° C. for up to 12 weeks.

Figure 8:
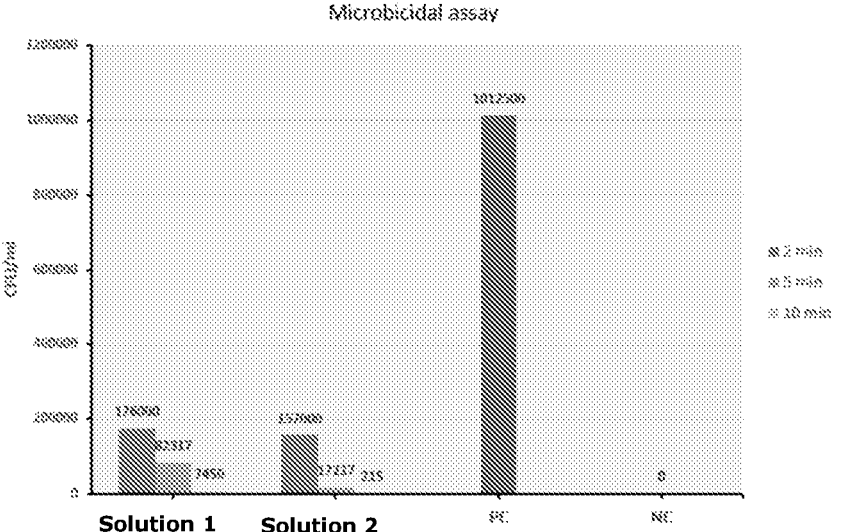
FIG. 8 depicts the *Mycobacterium ulcerans* bactericidal activity of a solution of the present invention by plating and counting of CFUs, as described in Example 6, with particular application to Buruli Ulcers.

Results shown in FIG. 8 are the mean CFUs for each dilution. After 2 minutes of exposure to the 2 Products, CFU counts were reduced by >80%. After 10 minutes, >99% for Solution 1 (40-70 ppm of free chlorine species) and >99.9 for Solution 2 (70-100 ppm of free chlorine species) of the bacteria were killed.

Example 7. In Vivo Testing for Covid-19 Viricidal Activity

The role of hypotonic acid oxidizing water containing Hypochlorous acid (HClO) meeting the specifications reported in example 1 has been assessed in an in vitro test in order to value the nasal tolerability and the efficacy of the product against SARS-Cov-2.

Methods:

Virus, Media, and Cells

SARS-CoV-2 virus stocks were prepared by growing virus in Vero 76 cells. Test media used was MEM supplemented with 2% FBS and 50 µg/mL gentamicin.

Viricidal Assay

Hypotonic acidic oxidizing solution meeting the specifications of Example 1 was tested at full strength, adding 90% sample to 10% virus solution by volume to achieve a final test concentration of 90%. SARS-CoV-2 virus stock was added to triplicate tubes and media only was added to one tube of each prepared concentration to serve as toxicity controls. Ethanol was tested in parallel as a positive control and water only to serve as the virus control.

Compound and virus were incubated at room temperature for two contact times of <1 minute and 3 minutes. Following the contact period, the solutions were neutralized by a 1/10 dilution in test media containing 10% FBS.

Virus Quantification

Neutralized samples were combined for quantification for the average of triplicate tests. Samples were serially diluted using eight half-log dilutions in test medium. Each dilution was added to 4 wells of a 96-well plate with 80-100% confluent Vero 76 cells. The toxicity controls were added to an additional 4 wells and 2 of these wells were infected with virus to serve as neutralization controls, ensuring that residual sample in the titer assay plated did not inhibit growth and detection of surviving virus. All plates were incubated at 37±2° C., 5% $CO_2$.

On day 6 post-infection plates were scored for presence or absence of viral cytopathic effect (CPE). The Reed-Muench method was used to determine end-point titers (50% cell culture infectious dose, $CCID_{50}$) of the samples, and the log reduction value (LRV) of the compound compared to the negative (water) control was calculated.

Controls

Virus controls were tested in water and the reduction of virus in test wells compared to virus controls calculated as the log reduction value (LRV). Toxicity controls were tested with media not containing virus to see if the samples were toxic to cells. Neutralization controls were tested to ensure that virus inactivation did not continue after the specified contact time, and that residual sample in the titer assay plates did not inhibit growth and detection of surviving virus. This was done by adding toxicity samples to titer test plates then spiking each well with a low amount of virus that would produce an observable amount of CPE during the incubation period.

Results:

Virus titers and LRV of Hypotonic acidic oxidizing Solution containing Hypochlorous acid (HClO) against SARS-CoV-2 are shown in TABLE 8:

TABLE 8

| | Concentration | Contact Time | Virus Titer[c] | LRV[b] |
|---|---|---|---|---|
| Acidic Super Oxidizing Solution | 90% | <1 min | <0.7 | >2.8 |

TABLE 8-continued

| | Concen- tration | Contact Time | Virus Titer[c] | LRV[b] |
|---|---|---|---|---|
| Ethanol | 63% | <1 min | <1.7 | >1.8 |
| Virus Control | n/a | <1 min | 3.5 | — |
| Acidic Super Oxidizing Solution | 90% | 3 min | <0.7 | >2.8 |
| Ethanol | 63% | 3 min | <1.7 | >1.8 |
| Virus Control | n/a | 3 min | 3.5 | — |

[a] $Log_{10}$ $CCID_{50}$ of virus per 0.1 mL
[b] LRV (log reduction value) is the reduction of virus compared to the virus control Viricidal activity was exhibited when solution was tested at 90% for a <1 minute and 3 minutes, reducing virus from 3.5 log CCID50 per 0.1 mL in virus controls to below the limit of detection of 0.7 logs (>99.8%). Further testing may be warranted to evaluate reproducibility and possibly activity at lower concentrations.

Neutralization controls demonstrated that residual sample did not inhibit virus growth and detection in the endpoint titer assays in wells that did not have cytotoxicity. Positive controls performed as expected, although ethanol was toxic to cells in the 1/10 dilution, limiting the detection of virus to <1.7 log CCID50 per 0.1 mL.

Example 7. Nasal Irritation Study

The objective of this nasal irritation test was to assess the possible irritation potential of the Hypotonic, acidic oxidizing solution containing Hypochlorous Acid when the test species New Zealand white rabbits were administered with test item twice daily for five consecutive days.

Study Design

Test item was intranasally applied at 200 μL/nostril and 500 μL/nostril using a 1 mL syringe fitted with MAD® (Mucosal Atomization Device), in each nostril twice a day at the interval of 4 hours for 5 consecutive days. In addition, physiological saline (500 μL/nostril) was applied to control group animals.

Methods

Rabbits were observed for general clinical signs, morbidity and mortality twice daily pre-dose (before first application) and post-dose (after the last application) on treatment days and once daily on non-treatment days. The local reactions at the site of application were examined twice daily on all application days i.e., before first application and after each day's last application (approximately 30 minutes post application) and once daily on non-treatment days. The local reaction was visually observed using a pen torch. The local reactions were evaluated as per the method of Draize (1959). All animals were euthanized after 24 hours of last application (Day 6) and subjected to detailed gross pathological examination. The animals were examined carefully for external abnormalities. The application sites (nostrils) from all the animals along with the surrounding tissues were examined macroscopically. The thoracic and abdominal cavities were cut open and a thorough examination of the organs was carried out to detect abnormalities. Histopathological examination was carried out on the nose of all animals. 4 levels of transverse sections of the nose (site of application) were examined microscopically. The tissues were processed for routine paraffin embedding and 5-micron sections were stained with Hematoxylin and Eosin stain. The tissue sections were evaluated, and scores were recorded as per method B.3 of ISO 10993-10 and irritation index was calculated as per method B.4 of ISO 10993-10.

Results

There were no clinical signs or pre-terminal deaths, and no effect on body weights. No local reaction was observed during the macroscopic examination at the site of application. Approximately 24 h after the last application, all animals were euthanized, and nasal mucosa from the lower edge of the inferior turbinate and nasal septal mucosa of the nasal cavity from all animals were collected, gross observation was recorded and processed for histopathology. There were no gross lesions in any of the tested animal at necropsy. Microscopic evaluation of nasal mucosa as per method B.3 and B.4 of ISO 10993-10, exhibited an irritation index of 0 and 0.083 for the 200 μL/nostril and 500 μL/nostril dose groups respectively (TABLE 9).

TABLE 9

| | Sex MALES | | |
|---|---|---|---|
| | Group No. | | |
| | G1 (saline) | G2 | G3 |
| | Dose Volume per Application | | |
| | 500 μL/ Nostril | 200 μL/ Nostril | 500 μL/ Nostril |
| No. of rabbits | 3 | 3 | 3 |
| Group severity grade average | 0.167 | 0.167 | 0.25 |
| Irritation index | | 0 | 0.083 |

Irritation Index: 0-None; 1 to 4-Minimal; 5 to 8-Mild; 9 to 11-Moderate; 12 to 16-Severe

CONCLUSION

Based on the above results its inferred that twice daily nasal administration of Hypotonic, acidic oxidizing solution containing Hypochlorous Acid to New Zealand White Rabbits at dose levels of 200 μL/nostril and 500 μL/nostril is "non-irritating" to nasal mucosa of New Zealand White Rabbits.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of treating a wound caused by Epidermolysis Bullosa ("EB") in a patient in need thereof comprising topically applying to said wound a therapeutically effective amount of a hypotonic, acid oxidizing, aqueous solution comprising a pH of from 2.5 to 6, a chloride content of less than 400 mg/L, and a free chlorine content of 20-140 mg/L, wherein said free chlorine content comprises ≥90 w/w % of hypochlorous acid (HClO), ≤10 w/w % of chlorine ($Cl_2$), and ≤3 w/w % of hypochlorite (ClO⁻).

2. The method of claim 1, wherein said wound is selected from the group consisting of skin blisters, mucosal blisters, scalp blistering, scarring alopecia, atrophic scarring, hyperkeratosis, milia, tooth decay, dysphagia, itchy skin, painful skin, and tearing.

3. The method of claim 1, wherein said wound is selected from the group consisting of skin and mucosa blisters and tearing.

4. The method of claim 1, wherein said patient is suffering from an elevation in matrix metalloproteinase-2 (MMP2) and matrix metalloproteinase-9 (MMP9) activity and said administration reduces said elevation.

5. The method of claim 1, further comprising administering to said patient a treatment selected from the group consisting of a topical dressing, aluminum chloride, cyproheptadine, a keratolytic, and a topical softening agent.

6. The method of claim 1, wherein said administration further treats any bacterial infection secondary to said Epidermolysis Bullosa.

7. The method of claim 1, wherein said patient is suffering from one or more biochemical abnormalities selected from nuclear factor kappa B (NF-$\hat{k}$B) signaling, nuclear factor erythroid 2-related factor 2 (Nrf2) activity, interleukin-1 (IL-1) activity, granulocyte macrophage colony-stimulating factor (GM-CSF) activity, interleukin-6 (IL-6) activity, MMP2, MMP9, tumor necrosis factor-alpha (TNF-$\alpha$) activity, keratinocyte growth factor (KGF) expression, transforming growth factor beta 2 (TGF$\beta$2) expression, transforming growth factor beta 1 (TGF$\beta$1) expression, and small interfering ATPase secretory pathway Ca2$^+$ transporting 1 (siATP2C1) keratinocyte proliferation, and said administration treats one or more of said biochemical abnormalities.

8. The method of claim 1, wherein said composition is administered to an affected topical surface on the body as a spray at 50-500 $\mu$L per actuation from a pump spray device.

9. The method of claim 1, wherein said composition is administered to an affected topical surface on the body as a spray at 50-500 $\mu$L per actuation from a pump spray device, and allowed to air dry without physical intervention.

10. The method of claim 1, wherein said composition is administered to an affected topical surface on the body as a spray at 50-500 $\mu$L per actuation from a pump spray device, and allowed to air dry without physical intervention followed by topical administration of a secondary treatment.

11. The method of claim 1, wherein said composition has a pH of from 2.5 to 4.5, a chloride content of $\leq$300 mg/L, and an oxidation reduction potential (ORP) of from 850 to 1350 mV.

12. The method of claim 1, wherein said composition comprises:

a. a chloride content of less than 250 mg/L;

b. a pH of from 2.5 to 4;

c. an ORP of from 850 to 1350 mV; and d. a free chlorine content of from 25 to 120 mg/L, comprising $\geq$92.5 w/w % of HClO, $\leq$7.5 w/w % of Cl$_2$, and <1 w/w % or 0 w/w % of ClO$^-$.

13. The method of claim 1, wherein said composition comprises:

a. a chloride content of less than 200 mg/L;

b. a pH of from 2.5 to 3;

c. an ORP of from 1000 to 1300 mV; and d. a free chlorine content of from 40 to 100 mg/L, comprising $\geq$95 w/w % of HClO, $\leq$5 w/w % of Cl$_2$, and <0.1 w/w % or 0 w/w % of ClO$^-$.

14. The method of claim 11, wherein said composition is administered as a spray at 50-500 $\mu$L per actuation from a pump spray device.

15. The method of claim 11, wherein said composition is administered as a spray at 50-500 $\mu$L per actuation from a pump spray device, and allowed to air dry without physical intervention.

16. The method of claim 11, wherein said composition is administered to an affected topical surface on the body as a spray at 50-500 $\mu$L per actuation from a pump spray device, and allowed to air dry without physical intervention followed by topical administration of a secondary treatment.

17. The method of claim 12, wherein said composition is administered as a spray at 50-500 $\mu$L per actuation from a pump spray device.

18. The method of claim 12, wherein said composition is administered as a spray at 50-500 $\mu$L per actuation from a pump spray device, and allowed to air dry without physical intervention.

19. The method of claim 12, wherein said composition is administered to an affected topical surface on the body as a spray at 50-500 $\mu$L per actuation from a pump spray device, and allowed to air dry without physical intervention followed by topical administration of a secondary treatment.

20. The method of claim 13, wherein said composition is administered as a spray at 50-500 $\mu$L per actuation from a pump spray device.

21. The method of claim 13, wherein said composition is administered as a spray at 50-500 $\mu$L per actuation from a pump spray device, and allowed to air dry without physical intervention.

22. The method of claim 13, wherein said composition is administered to an affected topical surface on the body as a spray at 50-500 $\mu$L per actuation from a pump spray device, and allowed to air dry without physical intervention followed by topical administration of a secondary treatment.

* * * * *